United States Patent
Takayama et al.

[11] Patent Number: 6,136,810
[45] Date of Patent: Oct. 24, 2000

[54] PYRIDO[2,3-D]PYRIMIDINE DERIVATIVES AND PHARMACEUTICAL COMPOSITIONS THEREOF

[75] Inventors: Kazuhisa Takayama; Hiroyuki Hisamichi; Masahiro Iwata; Hideki Kubota; Motonori Aoki, all of Ibaraki, Japan

[73] Assignee: Yamanouchi Pharmaceutical Co., Ltd., Tokyo, Japan

[21] Appl. No.: 09/066,370

[22] PCT Filed: Nov. 20, 1996

[86] PCT No.: PCT/JP96/03389

§ 371 Date: Apr. 30, 1998

§ 102(e) Date: Apr. 30, 1998

[87] PCT Pub. No.: WO97/19078

PCT Pub. Date: May 29, 1997

[30] Foreign Application Priority Data

| Nov. 21, 1995 | [JP] | Japan | 7-303065 |
| Jan. 19, 1996 | [JP] | Japan | 8-007725 |
| Feb. 29, 1996 | [JP] | Japan | 8-043853 |
| Jun. 4, 1996 | [JP] | Japan | 8-141868 |

[51] Int. Cl.[7] ....................... A61K 31/505; C07D 471/04
[52] U.S. Cl. ............................ 514/258; 546/279
[58] Field of Search ............................ 544/279; 514/258

[56] References Cited

U.S. PATENT DOCUMENTS

| 3,709,888 | 1/1973 | Hardtmann | 260/256.4 |
| 3,758,475 | 9/1973 | Hardtmann et al. | 260/256.4 |
| 3,853,898 | 12/1974 | Hardtmann et al. | 260/296 |
| 4,224,328 | 9/1980 | Takesue et al. | 424/251 |

FOREIGN PATENT DOCUMENTS

| 37 31/87 | 4/1988 | Hungary . |
| 9303774A | 9/1994 | Hungary . |
| WO 88/012708 | 2/1988 | WIPO . |

OTHER PUBLICATIONS

The effect of a novel orally active selective PDE4 isoenzyme inhibitor (CDP840) on alergen–induced responses in asthmatic subjects, P.L. Harbinson, et al., European Respiratory Journal, ISSN 0903—1936; p. 10: 1008–1014 (1997).

Acute versus chronic administration of posphodiesterase inhibitors on allergen–induced pulmonary cell influx in sensitized guinea–pigs, Katharine H. Banner & Clive P. Page, British Journal of Pharmacology, 114; p. 93–98 (1995).

Primary Examiner—Richard L. Raymond
Attorney, Agent, or Firm—Sughrue, Mion, Zinn, Macpeak & Seas, PLLC

[57] ABSTRACT

This invention relates to compounds (I) or pharmaceutically acceptable salts thereof, having a function to inhibit type IV phosphodiesterase (PDE)

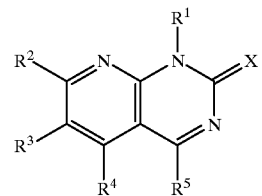

(I)

[X: an oxygen atom or a sulfur atom, $R^1$: a lower alkyl group, a cycloalkyl-lower alkyl group or a cycloalkyl group, $R^2$: a hydrogen atom, a halogen atom, a lower alkyl group, a halogeno-lower alkyl group, a hydroxy-lower alkyl group, a mercapto-lower alkyl group, a lower alkoxy-lower alkyl group, a lower alkylthio-lower alkyl group, a lower alkanoyloxy-lower alkyl group, a lower alkanoylthio-lower alkyl group, a lower alkanoyl-lower alkyl group, a hydroxyimino-lower alkyl group, a lower alkoxyimino-lower alkyl group, a cycloalkyl group, an aryl group or a lower alkanoyl group, $R^3$: a hydrogen atom, a halogen atom or a lower alkyl group, $R^4$: a hydrogen atom or a lower alkyl group, $R^5$: a cycloalkyl group; a naphthyl group substituted; a five- or six-membered monocyclic hetero ring group having 1 to 4 hetero atoms selected from nitrogen atom, oxygen atom and sulfur atom; or a group represented by the formula

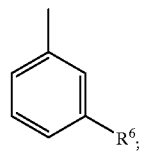

amd $F^6$: a halogen atom, a lower alkyl group, a halogeno-lower alkyl group, a hydroxyl group, a lower alkoxy group, a cyano group or a nitro group].

11 Claims, No Drawings

6,136,810

PYRIDO[2,3-D]PYRIMIDINE DERIVATIVES AND PHARMACEUTICAL COMPOSITIONS THEREOF

This application is a 371 of PCT/JP96/03389, filed Nov. 20, 1996.

TECHNICAL FIELD

This invention relates to novel pyrido[2,3-d]pyrimidine derivatives useful as medicines, particularly as type IV phosphodiesterase inhibitors, pharmaceutically acceptable salts thereof, pharmaceutical compositions thereof, use thereof for the production of medicaments and a preventing or treating method in which an effective amount thereof is administered.

BACKGROUND ART

Asthma is a respiratory disease which repeats stridor and attack due to airway contraction. The number of the asthma patients has been increasing constantly and is considered to further increase in the future.

Main morbid states of asthma are a) sudden contraction of smooth muscle which surrounds the airway and b) inflammatory reaction caused by the activation of infiltrative cells in respiratory organs including the lungs. Therefore, it is considered that inhibition of the airway smooth muscle contraction and inhibition or prevention of the activation of infiltrative celis are considered to be effective means for the treatment of symptoms of asthma.

For the treatment of asthma, xanthine derivatives such as aminophylline, theophylline and β-stimulators such as procaterol are now mainly used as drugs which remit symptoms of asthma by dilating the bronchus. The action mechanism of these compounds is that they inhibit contraction of airway smooth muscle. through the increment of the concentration of cyclic adenosine 3',5'-monophosphate (cAMP) in the cells of the airway smooth muscle, which is effected by the activation of adenylate cyclase as a cAMP producing enzyme or by the inhibition of phosphodiesterase (PDE) as a cAMP hydrolyzing enzyme [*Thorax*, 46, 512–523 (991)].

However, xanthine derivatives generate systemic side effects such as decrease in blood pressure, cardiotonic action and the like [*J. Cyclic Nucleotide and Protein Phosphorylation Res.*, 10, 551–564 (1985)] and, therefore, it is necessary to monitor its concentration in blood in order to prevent these systemic side effects. In addition, xanthine derivatives do not exert clear effect against asthma when it involves infiltration of inflammatory cells.

On the other hand, it is known that β-stimulators generate side effects such as finger tremor, palpitation and the like, when the dose is increased because of their aptness to generate desensitization.

Studies conducted thereafter have revealed that the DPE, an enzyme which hydrolyses cAMP, is divided into at least four different types of I to IV having different distributions and functions [*Pharmacological Therapy*, 51, 13–33 (1991)]. Particularly, the type IV PDE hydrolyses cAMP in a specific fashion without acting upon cyclic guanosine 3',5'-monophosphate (cGMP) among nucleotides, and its presence is found in both airway smooth muscle and infiltrative cells.

Incidentally, PDE V is known as an enzyme which degrades cGMP.

Concentration of cAMP in cells is set by the balance of the cAMP production rate by adenylate cyclase and the cAMP hydrolyzation rate by PDE. In consequence, intracellular cAMP concentration can be increased by stimulating adenylate cyclase or inhibiting PDE. Increase in the intracellular cAMP concentration induces inhibition of contraction of the airway smooth muscle and inhibition of the activation of inflammatory cells [*Clin. Exp. Allergy*, 22, 337–344 (1992), *Drugs of the Future*, 17, 799–807 (1992)].

Also, it has been reported that a type IV PDE inhibitor shows an action to inhibit eosinophiles infiltration by antigen and platelet activating factor in guinea pigs [*Eur. J. Pharmacol.*, 255, 253–256 (1994)] and inhibits release of cytotoxic proteins (MBP, ECP) from eosinophiles [*Br. J. Pharmacol.*, 115, 39–47 (1995)]. It has been reported also that it shows an action to inhibit contraction of the airway smooth muscle caused by contractile substances (histamine, LTD$_4$, methacholine) [*Br. T. Pharmacol.*, 113, 1423–1431 (1994)], inhibits production of IL-4 which is a member of cytokine which is considered to be concerned deeply in asthma [*J. Invest. Dermatol.*, 100, 681–684 (1993)], expresses an action to inhibit acceleration of vascular permeability in the airway [*Fundam. Clin. Pharmacol.*, 6, 247–249 (1992)] and shows an action to inhibit airway hyperreactivity [*Eur. J. Pharmacol.*, 275, 75–82 (1995)].

In consequence, an agent having excellent activity to inhibit type IV PDE is expected as an anti-asthma drug which hardly generates side effects and can remit or prevent asthmatic symptoms effectively.

It is known that a compound having a quinazolin-2-one structure has PDE inhibiting activity which is not limited to the type IV (cf. International Patent Publication 94/12499), but its structure is different from that of the pyrido[2,3-d] pyrimidine compound provided by the present invention.

On the other hand, a compound having a 4-phenylpyrido [2,3-d]pyrimidin-2-one structure has been reported by G. E. Hardtmann et al. in U.S. Pat. No. 3,758,475. In this patent, a compound having anti-inflammatory activity, which can be recognized by a carrageenin-induced edema suppression test, is shown by the following general formula:

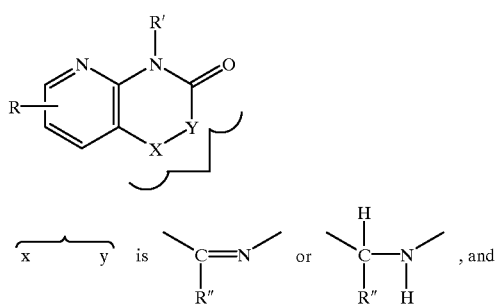

wherein

R is hydrogen or lower alkyl of 1 to 5 carbon atoms, e.g., methyl;

R' is lower alkyl of 1 to 6 carbon atoms, e.g., methyl, ethyl, propyl, isopropyl, t-butyl, etc.; allyl; methallyl; propargyl; or cycloalkyl of 3 to 6 carbon atoms, e.g., cyclopropyl; and R" is phenyl or substituted phenyl of the formula:

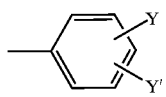

and

Y represents halo of atomic weight of from 19 to 80; lower alkyl of 1 to 4 carbon atoms; or lower alkoxy of 1 to 4 carbon atoms; and Y' represents hydrogen, halo, lower alkyl or lower alkoxy (all as defined for Y).

Similar anti-inflammatory compound has been reported also by G. E. Hardtmann et al. in *J. Med. Chem.* (Vol. 17, No. 16, 636–639, 1974).

Also, a method for the inhibition of platelet agglutination in which a 1-substituted-4-arylpyrido[2,3-d]pyrimidin-2-one, a compound similar to the aforementioned compound, is administered has been reported [cf. an unexamined published Japanese patent application (kokai) No. 53-94040].

Some of the compounds provided by the present invention are included in the general formula shown in the aforementioned U.S. Patent, because they correspond to the compound of the formula in which R is a lower alkyl group, R' is a lower alkyl group or a $C_{3-6}$ cycloalkyl group and R" is a phenyl group having a halogen atom, a lower alkyl group or a lower alkoxy group on its meta position.

However, there are no illustrative descriptions in Examples and other parts of the U.S. Patent about a compound which has a halogen atom or a lower alkyl group only at the meta position of phenyl group and also has a lower alkyl group at the 7-position of pyrido[2,3-d]pyrimidine. In addition, the aforementioned U.S. Patent describes only about anti-inflammatory activity and does not describe or suggest about inhibitory action against the type IV PDE and anti-asthma action.

DISCLOSURE OF THE INVENTION

The inventors of the present invention have conducted intensive studies on compounds which show inhibitory activity against type IV PDE and accomplished the present invention based on the finding that compounds represented by the following general formula (I) have excellent type IV PDE inhibiting activity.

Thus, according to the present invention, there is provided a pyrido[2,3-d]pyrimidine derivative represented by the following general formula (I) or a pharmaceutically acceptable salt thereof:

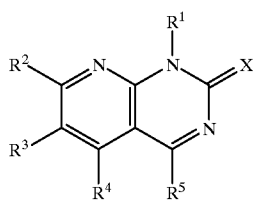

(I)

[Each symbol in the formula represents the following meaning;

X: an oxygen atom or a sulfur atom, $R^1$: a lower alkyl group, a cycloalkyl-lower alkyl group or a cycloalkyl group, $R^2$: a hydrogen atom, a halogen atom, a lower alkyl group, a halogeno-lower alkyl group, a hydroxy-lower alkyl group, a mercapto-lower alkyl group, a lower alkoxy-lower alkyl group, a lower alkylthio-lower alkyl group, a lower alkanoyloxy-lower alkyl group, a lower alkanoylthio-lower alkyl group, a lower alkanoyl-lower alkyl group, a hydroxyimino-lower alkyl group, a lower alkoxyimino-lower alkyl group, a cycloalkyl group, an aryl group or a lower alkanoyl group, $R^3$: a hydrogen atom, a halogen atom or a lower alkyl group, $R^4$: a hydrogen atom or a lower alkyl group, $R^5$: a cycloalkyl group which may be substituted with the same group of $R^6$; a naphthyl group which may be substituted with the same group of $R^6$; a five- or six-membered monocyclic hetero ring group having 1 to 4 hetero atoms selected from nitrogen atom, oxygen atom and sulfur atom, which may be substituted with the same group of $R^6$ and which may be condensed with benzene ring; or a group represented by the formula

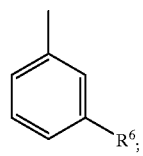

and $R^6$: a halogen atom, a lower alkyl group, a halogeno-lower alkyl group, a hydroxyl group, a lower alkoxy group, a cyano group or a nitro group, with the proviso that $R^2$ is a group other than hydrogen atom when $R^5$ is a group represented by the formula

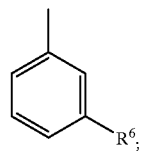

$R^6$ is a halogen atom, a lower alkyl group or a lower alkoxy group, $R^1$ is a lower alkyl group or a cycloalkyl group, $R^3$ and $R^4$ are both a hydrogen atom and X is an oxygen atom.]

Among compounds represented by the general formula (I), those in which X is an oxygen atom, $R^1$ is a lower alkyl group or a cycloalkyl group, $R^2$ is a lower alkyl group, $R^3$ and $R^4$ are both a hydrogen atom, $R^5$ is a group represented by the formula

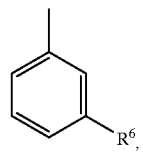

and $R^6$ is a halogen atom, a lower alkyl group or a lower alkoxy group are included in the general formula shown in the aforementioned U.S. Patent.

However, these compounds of the present invention are characterized in terms of the chemical structure that a halogen atom, a lower alkyl group or a lower alkoxy group is introduced only into the meta position (3-position) of the 4-position phenyl group of the 1-substituted-4-phenylpyrido[2,3-d]pyrimidin-2(1H)-one structure, and that an alkyl group is introduced into the 7-position.

Such compounds having specified substituents at the specified positions are novel, because they are not illustratively described in the aforementioned U.S. Patent. Also, such compounds have a pharmacological feature in that they exert markedly excellent action in terms of type IV PDE inhibiting activity which is not disclosed or suggested in the aforementioned U.S. Patent.

Particularly, it was confirmed that a pyrido[2,3-d]pyrimidine derivative represented by the following general formula (II) or a pharmaceutically acceptable salt thereof exerts markedly excellent action upon type IV PDE in comparison with the inherent effect of the similar compounds disclosed in the aforementioned U.S. Patent.

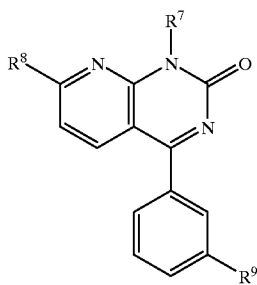

(II)

[In the above formula, $R^7$ represents methyl, ethyl, propyl or isopropyl group, $R^8$ represents methyl, ethyl, propyl or isopropyl group, and $R^9$ represents chlorine or bromine atom or methyl group.]

On the other hand, a pyrido[2,3-d]pyrimidine derivative represented by the following general formula (III), resulting from the exclusion of the compounds to be included in the general formula of the aforementioned U.S. Patent from the compound (I) of the present invention, or a pharmaceutically acceptable salt thereof is a novel compound which is not disclosed in the prior art references.

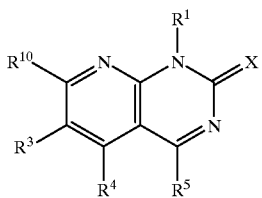

(III)

[In the above formula, X, $R^1$, $R^3$, $R^4$ and R5 are as defined in the foregoing, and $R^{10}$ represents a hydrogen atom, a halogen atom, a lower alkyl group, a halogeno-lower alkyl group, a hydroxy-lower alkyl group, a mercapto-lower alkyl group, a lower alkoxy-lower alkyl group, a lower alkylthio-lower alkyl group, a lower alkanoyloxy-lower alkyl group, a lower alkanoylthio-lower alkyl group, a lower alkanoyl-lower alkyl group, a hydroxyimino-lower alkyl group, a lower alkoxyimino-lower alkyl group, a cycloalkyl group, an aryl group or a lower alkanoyl group, with the proviso that $R^{10}$ is a group other than a hydrogen atom and a lower alkyl group when $R^5$ is a group represented by the formula

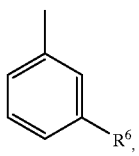

$R^6$ is a halogen atom, a lower alkyl group or a lower alkoxy group, $R^1$ is a lower alkyl group or a cycloalkyl group, $R^3$ and $R^4$ are both a hydrogen atom and X is an oxygen atom.]

The compound (III) of the present invention or a pharmaceutically acceptable salt thereof has a chemical structural feature in that the pyrido[2,3-d]pyrimidine skeleton has a specified alkyl-based group on its 1-position, an oxo or thioxo group on its 2-position, a specified ring-based group on its 4-position and specified substituents on its 5-, 6- and 7-positions and a pharmacological feature in that it has a selective inhibition activity against type IV PDE.

Particularly, the invention of compound (III) is characterized in that a compound having a pyrido[2,3-d]pyrimidine structure is provided for the first time as a type IV PDE inhibitor.

Particularly preferred among the compounds of the present invention are compounds represented by the general formulae (II) and (III) and pharmaceutically acceptable salts thereof. Among compounds of (II), particularly preferred are those in which Rs is methyl or ethyl, more preferably those in which $R^8$ is the said group and $R^7$ is ethyl or propyl. Illustrative examples of most preferred compounds are as follows.

4-(3-Chlorophenyl)-1,7-diethylpyrido[2,3-d]pyrimidin-2(1H)-one, 4-(3-bromophenyl)-1,7-diethylpyrido[2,3-dapyrimidin-2(1H)-one, 4-(3-chlorophenyl)-1-ethyl-7-methylpyrido[2,3-d]pyrimidin-2(1H)-one, 4-(3-bromophenyl)-1-ethyl-7-methylpyrido[2,3-d]pyrimidin-2(1H)-one, 1-ethyl-7-methyl-4-(3-methylphenyl)pyrido[2,3-d]pyrimidin-2(1H)-one and 1,7-diethyl-4-(3-methylphenyl)pyrido[2,3-d]pyrimidin-2(1H)-one.

Among the compounds of (III), particularly preferred are those in which $R^{10}$ is a hydrogen atom, a lower alkyl group, a halogeno-lower alkyl group, a hydroxy-lower alkyl group, a mercapto-lower alkyl group, a lower alkoxy-lower alkyl group, a lower alkylthio-lower alkyl group, a lower alkanoyloxy-lower alkyl group, a lower alkanoylthio-lower alkyl group, a hydroxyimino-lower alkyl group, a cycloalkyl group, an aryl group or a lower alkanoyl group, more preferably those in which $R^{10}$ is a hydrogen atom, a lower alkyl group, a halogeno-lower alkyl group, a hydroxy-lower alkyl group, a lower alkoxy-lower alkyl group, a lower alkanoyloxy-lower alkyl group, a lower alkanoylthio-lower alkyl group, a hydroxyimino-lower alkyl group, a cycloalkyl group, an aryl group or a lower alkanoyl group. More particularly, those in which $R^{10}$ is the just described group; $R^4$ is hydrogen atom; $R^5$ is (1) a cycloalkyl group which may be substituted with a lower alkyl group, (2) a naphthyl group, (3) a five- or six-membered monocyclic hetero ring group having 1 to 4 hetero atoms selected from nitrogen, oxygen and sulfur atoms or (4) a group represented by the formula

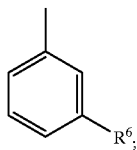

and $R^6$ is a halogen atom, a lower alkyl group, a halogeno-lower alkyl group, a lower alkoxy group, a cyano group or a nitro group are preferred, and those in which $R^1$ is a lower alkyl group or a cycloalkyl-lower alkyl group, $R^{10}$ is a lower alkyl group, a halogeno-lower alkyl group, a hydroxy-lower alkyl group, a lower alkanoylthio-lower alkyl group, a hydroxyimino-lower alkyl group, a cycloalkyl group or a lower alkanoyl group, $R^3$ and $R^4$ are both a hydrogen atom, $R^5$ is a cycloalkyl group which may be substituted with a lower alkyl group or a group represented by the formula

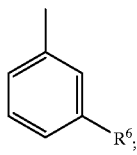

and $R^6$ is a halogen atom, a lower alkyl group or a nitro group are more preferred.

Illustrative examples of the most preferred compounds are as follows.

4-Cyclohexyl-1-ethyl-7-methylpyrido[2,3-d]pyrimidin-2 (1H)-one, 4-(3-chlorophenyl)-1-ethyl-7-(1-hydroxyethyl) pyrido[2,3-d]pyrimidin-2(1H)-one, 4-(3-chlorophenyl)-7-cyclopropyl-1-ethylpyrido[2,3-d]pyrimidin-2(1H)-one, 1-ethyl-7-methyl-4-(3-methylcyclohexyl)pyrido[2,3-d]pyrimidin-2(1H)-one, 1,7-diethyl-4-(3-methylcyclohexyl) pyrido[2,3-d]pyrimidin-2(1H)-one, 4-(3-chlorophenyl)-1-ethyl-7-methylpyrido[2,3-d]pyrimidin-2(1H)-thione, 1-cyclopropylmethyl-7-methyl-4-(3-methylphenyl)pyrido [2,3-d]pyrimidin-2(1H)-one, 4-cyclohexyl-1,7-diethylpyrido[2,3-d]pyrimidin-2(1H)-one, 4-(3-chlorophenyl)-1-ethyl-7-hydroxyiminopyrido[2,3-d] pyrimidin-2(1H)-one, 7-(1-acetylthioethyl)-4-(3-chlorophenyl)-1-ethylpyrido[2,3-d]pyrimidin-2(1H)-one and 1,7-diethyl-4-(3-chlorophenyl)pyrido[2,3-d]pyrimidin-2(1H)-thione.

The present invention also includes a pharmaceutical composition which comprises the compound (I) or a pharmaceutically acceptable salt thereof, preferably the compound (III) or a pharmaceutically acceptable salt thereof, and a pharmaceutically acceptable carrier. Embodiments of the pharmaceutical composition includes a type IV PDE inhibitor which contains the compound (I), preferably the compound (III), or a pharmaceutically acceptable salt thereof, more particularly an agent for use in the prevention or treatment of respiratory diseases in which type IV PDE is concerned, especially bronchial asthma.

Also included in the present invention is a type IV PDE inhibitor which contains the compound (II) or a pharmaceutically acceptable salt thereof, more particularly an agent for use in the prevention or treatment of respiratory diseases in which type IV PDE is concerned, especially bronchial asthma.

Also included in the present invention is the use of the compound (I), preferably Compound (II) or (III), or a pharmaceutically acceptable salt thereof for the production of an agent for use in the prevention or treatment of diseases in which acceleration of type IV PDE is concerned, especially respiratory diseases more especially bronchial asthma, or a method for the prevention and treatment of said disease in which an effective amount of said compound is administered to patients who contracted or have a possibility of contracting said disease.

The following describes the compound of the present invention further in detail.

Unless otherwise noted, the term "lower" as used in the definition of the general formulae of the present invention means a straight or branched carbon chain having 1 to 6 carbon atoms.

Illustrative examples of the "lower alkyl group" include straight or branched $C_{1-6}$ alkyl groups such as methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl and the like. Of these groups, $C_{1-4}$ alkyl groups such as methyl, ethyl, propyl, isopropyl, butyl and the like are preferred, and $C_{1-3}$ alkyl groups such as methyl, ethyl, propyl, isopropyl and the like are particularly preferred. As the lower alkyl group of $R^1$, $C_{1-14}$ alkyl groups, particularly $C_{2-3}$ alkyl groups, are preferred, and $C_{1-3}$ alkyl groups, especially methyl and ethyl groups, are preferred as the lower alkyl groups of $R^2$.

Illustrative examples of the "lower alkoxy group" include straight or branched $C_{1-6}$ alkoxy groups such as methoxy, ethoxy, propoxy, isopropoxy, butoxy, isobutoxy, sec-butoxy, tert-butoxy, pentyloxy (amyloxy), isopentyloxy, tert-pentyloxy, neopentyloxy, 2-methylbutoxy, 1,2-dimethylpropoxy, 1-ethylpropoxy, hexyloxy and the like, of which methoxy and ethoxy groups are preferred.

The term "lower alkylthio group" as used herein means a group in which the hydrogen atom of the thiol group is substituted with the aforementioned lower alkyl group, and its illustrative examples include straight or branched $C_{1-6}$ alkylthio groups such as methylthio, ethylthio, propylthio, isopropylthio, butylthio, isobutylthio, sec-butylthio, tert-butylthio, pentylthio, isopentylthio, neopentylthio, tert-pentylthio, 2-methylbutylthio, 1,2-dimethylpropylthio, 1-ethylpropylthio, hexylthio and the like, of which methylthio and ethylthio groups are preferred.

Illustrative examples of "lower alkanoyl group" include straight or branched $C_{1-16}$ alkanoyl groups such as formyl, acetyl, propionyl, butylyl, isobutylyl, valeryl, isovaleryl, pivaloyl and the like, of which formyl, acetyl and propionyl groups are preferred.

The "lower alkanoyloxy group" is a group resulting from the esterification of an alcohol and a lower carboxylic acid, and its illustrative examples include straight or branched $C_{1-6}$ alkanoyloxy groups such as formyloxy, acetoxy, propionyloxy, butylyloxy, isobutylyloxy, valeryloxy, pivaloyloxy and the like.

The "lower alkanoylthio group" is a group resulting from the thioesterification of a thiol and a lower carboxylic acid, and its illustrative examples include straight or branched $C_{1-6}$ alkanoylthio groups such as formylthio, acetylthio, propionylthio, butylylthio, isobutylylthio, valerylthio, pivaloylthio and the like.

Illustrative examples of "cycloalkyl group" include those which have 3 to 8 carbon atoms, such as cyclopropyl, in cyclobutyl, cyclopentyl, cyclohexyl, cycloheptyl, and cyclooctyl. A cyclopropyl group is particularly preferred as the cycloalkyl group of "a cycloalkyl-lower alkyl group" of $R^1$ and that of $R^2$. Also, a cyclohexyl group is particularly preferred as the cycloalkyl group of "a cycloalkyl group which may be substituted" of $R^5$.

The term "aryl group" means an aromatic hydrocarbon group preferably having 6 to 14 carbon atoms. Its preferred illustrative examples include phenyl, tolyl, xylyl, biphenyl, naphthyl, indenyl, anthryl and phenanthryl groups, more preferably phenyl and naphthyl groups, most preferably a phenyl group.

Examples of the "halogen atom" include fluorine, chlorine, bromine and iodine atoms, and chlorine and bromine atoms are particularly preferred as the substituent for ring systems, and fluorine, chlorine and bromine atoms as the substituent for alkyl chains.

The aforementioned substituted "lower alkyl group" of $R^1$, $R^2_1$ $R^6$ or $R^{10}$, particularly $R^2$ or $R^{10}$, may be substituted with one to four (particularly one to three) various substituents and illustrative examples of such substituents respectively include a halogeno group, a hydroxyl group, a mercapto group, a lower alkoxy group, a lower alkylthio group, a lower alkanoyloxy group, a lower alkanoylthio group, a lower alkanoyl group, a hydroxyimino group, a lower alkoxyimino group and a cycloalkyl group. In this case, illustrative examples of the halogen atom which constitutes the "halogeno group" and the lower alkoxy, lower alkylthio, lower alkanoyloxy, lower alkanoylthio, lower alkanoyl and cycloalkyl groups include those described in the foregoing.

Illustrative examples of the "lower alkoxyimino group" include straight or branched $C_{1-6}$ alkoxyimino groups such as methoxyimino, ethoxyimino, propoxyimino, isopropoxyimino, butoxyimino, isobutoxyimino, tert-butoxyimino and the like.

In consequence, preferred illustrative examples of the substituted lower alkyl groups respectively include: trifluoromethyl, chloromethyl, bromomethyl, 2-chloroethyl, 1-chloroethyl, 2-bromoethyl, 1-bromoethyl and the like as the "halogeno-lower alkyl group"; hydroxymethyl, 2-hydroxyethyl, 1-hydroxyethyl and the like as the "hydroxy-lower alkyl group"; mercaptomethyl, 2-mercaptoethyl, 1-mercaptoethyl and the like as the "mercapto-lower alkyl group"; methoxymethyl, ethoxymethyl, 2-methoxyethyl, 1-methoxyethyl, dimethoxyethyl and the like as the "lower alkoxy-lower alkyl group"; methylthiomethyl, ethylthiomethyl, 2-methylthioethyl, 1-methylthioethyl and the like as the "lower alkylthio-lower alkyl group"; acetoxymethyl, 2-acetoxyethyl, 1-acetoxyethyl and the like as the "lower alkanoyloxy-lower alkyl group"; acetylthiomethyl, 2-acetylthioethyl, 1-acetylthioethyl and the like as the "lower alkanoylthio-lower alkyl group"; formylmethyl, acetonyl, 2-oxobutyl and the like as the "lower alkanoyl-lower alkyl group"; hydroxyiminomethyl, 2-hydroxyiminoethyl, 1-hydroxyiminoethyl and the like as the "hydroxyimino-lower alkyl group"; methoxyiminomethyl, ethoxyiminomethyl and the like as the "lower alkoxyimino-lower alkyl group"; and cyclopropylmethyl, cyclohexylmethyl, 2-cyclopropylethyl and the like as the "cycloalkyl-lower alkyl group".

Illustrative examples of the "five- or six-membered monocyclic hetero ring group having 1 to 4 hetero atoms selected from the group consisting of nitrogen atom, sulfur atom and oxygen atom, which may be condensed with benzene ring" include monocyclic hetero rings such as furyl, thienyl, pyrrolyl, imidazolyl, pyrazolyl, thiazolyl, isothiazolyl, oxazolyl, isoxazolyl, triazolyl, oxadiazolyl, thiadiazolyl, tetrazolyl, pyridyl, pyrimidinyl, pyridazinyl, pyrazinyl and the like, and these monocyclic hetero ring groups, together with benzene ring, may form condensed rings such as indolyl, indazolyl, benzofuranyl, isobenzofuranyl, benzothienyl, isoindolyl, isoquinolyl, chromenyl, quinolyl, quinazolinyl, benzimidazolyl, benzothiazolyl, benzoxazolyl, benzotriazolyl, benzoxadiazolyl, phthalazinyl, quinoxalinyl, cinnolinyl and the like. Bonding of these condensed rings to the 4-position of the pyrido[2,3-d]pyrimidine ring may be formed through any of the carbon and nitrogen atoms on the hetero ring or carbon atoms on the benzene ring. Of these monocyclic hetero rings, furyl, thienyl, pyrrolyl, imidazolyl, thiazolyl, pyridyl, pyrimidinyl, pyridazinyl and pyrazinyl groups are preferred, and thienyl, thiazolyl and pyridyl are more preferred.

When $R^5$ is a cycloalkyl group, a naphthyl group or a hetero ring group, the number of substituents to be substituted is not limited to one, more preferably one to three.

Compounds of the present invention may form salts. Pharmaceutically acceptable salts of the compound (I), particularly compounds (II) and (III), are included in the present invention, and examples of such salts include acid addition salts with inorganic acid (e.g., hydrochloric acid, hydrobromic acid, hydroiodic acid, sulfuric acid, nitric acid, phosphoric acid and the like) and with organic acids (e.g., formic acid, acetic acid, propionic acid, butyric acid, isobutyric acid, valeric acid, isovaleric acid, pivalic acid, oxalic acid, malonic acid, succinic acid, fumaric acid, maleic acid, lactic acid, citric acid, malic acid, tartaric acid, carbonic acid, methanesulfonic acid, ethanesulfonic acid, glutamic acid, aspartic acid and the like).

The compounds of the present invention exist in tautomer forms based on the presence of cyclic urea or thiourea having conjugated double bond. Also, depending on the type of substituents, it may exist in optical isomer forms based on the presence of asymmetric carbons and other isomer forms based on the presence of a cyclic ring, a hydroxyimino group and a lower alkoxyimino group. All of these isomers in separated form or mixtures thereof are included in the present invention.

In addition, the compounds of the present invention may be isolated in the form of hydrates, solvates with ethanol and the like or substances having various crystalline forms having polymorphism, depending on their physicochemical properties or production conditions. All of these hydrates, solvates with ethanol and the like and substances having various crystalline forms are also included in the present invention.

(Production Methods)

Compounds of the present invention and salts thereof can be produced by employing various synthetic methods, making use of the characteristics of their basic structure and types of substituents. The following describes their typical production methods.

In this connection, starting compounds or compounds of the present invention can be subjected to the synthetic reactions after protecting their functional groups with appropriate protective groups. Examples of such protective groups can be found, for example, in "*Protective Groups in Organic Synthesis*" 2nd edition, edited by Greene and Wuts, and these groups can be optionally used depending on each reaction condition.

In addition, an aldehyde compound may be obtained by the reaction using a corresponding acetal compound and the subsequent conversion into the aldehyde.

First Production Method (cyclization)

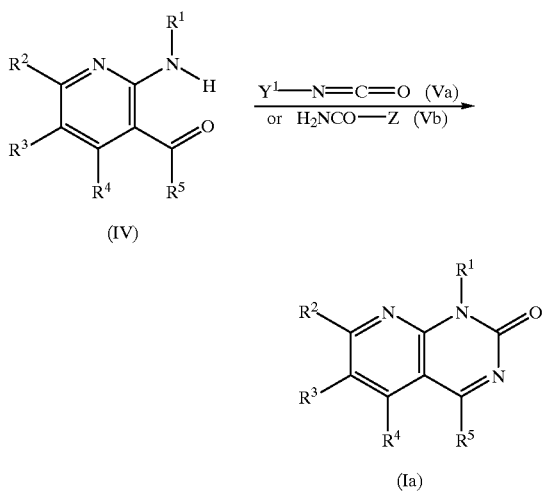

(In the above formulae, $R^1$, $R^2$, $R^3$, $R^4$ and $R^5$ are as defined in the foregoing, and $Y^1$ and Z represent leaving groups which are advantageous for this reaction.)

A compound (Ia) as one of the compounds of the present invention in which X is an oxo group can be produced by allowing a 2-aminopyridylketone derivative (IV) to react with an isocyanate represented by a general formula (Va) or a carbamate derivative represented by a general formula (Vb), thereby effecting cyclization.

Examples of the leaving group represented by $Y^1$ include halogenosulfonyl groups such as a chlorosulfonyl group and the like and tri-substituted silyl groups such as a trimethylsilyl group and the like.

Examples of the leaving group represented by Z include alkoxy groups (e.g., methoxy and ethoxy) and a phenoxy group.

The reaction in which an isocyanate is used is carried out in a solvent inert to the reaction which is selected, for example, from halogenated hydrocarbons (e.g., dichloromethane, dichloroethane, chloroform and the like), aromatic hydrocarbons (e.g., benzene, toluene, xylene and the like) and ethers (e.g., diethyl ether, tetrahydrofuran, dioxane and the like) at cooling temperature of −78° C. to 0° C., at cooling to room temperature, at room temperature or, as occasion demands, at room to heating temperature.

In carrying out the reaction, the compound (IV) and the isocyanate (Va) are used in equivalent molar amounts or either one is used in an excess amount, and the reaction may be carried out in the presence of a base such as triethylamine, diisopropylethylamine, N-methylmorpholine, N,N-dimethylaniline, pyridine, 4-(N,N-dimethylamino)pyridine, picoline, lutidine or the like which is sometimes advantageous in carrying out the reaction smoothly.

When the carbamate derivative represented by the general formula (Vb) is used in stead of the isocyanate (Va), it is advantageous to carry out the reaction in the presence of a Lewis acid such as zinc chloride, stannic chloride, titanium tetrachloride, boron trifluoride-ethyl ether or the like.

In this connection, a compound having a halogen atom at the 6-position is sometimes obtained as a by-product of this method.

The aforementioned starting compound (IV) can be obtained easily by synthesizing it by the production method of the following reaction scheme described in Reference Examples or a modified method thereof.

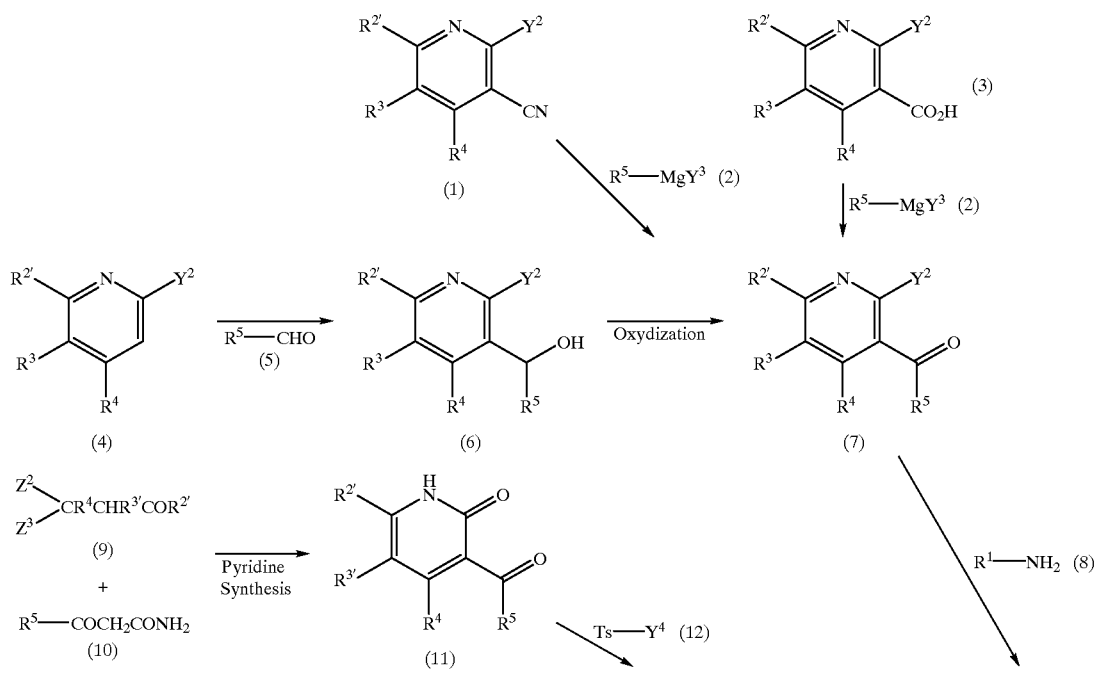

-continued

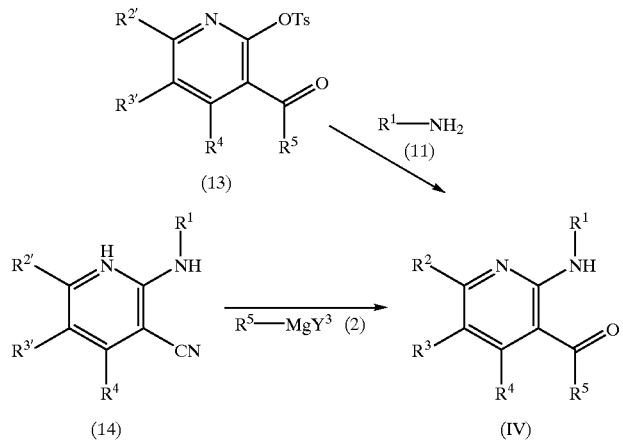

(In the above formulae, $R^1$, $R^7$, $R^3$, $R^4$ and $R^5$ are as defined in the foregoing, and other symbols represent as follows;

$R^{2'}$: the same group of $R^2$, which may be protected, $R^{3'}$: the same group of $R^3$, excluding halogen atoms, $Y^2$, $Y^3$ and $Y^4$: the same or different from one another, and each represents a halogen atom, $Z^2$ and $Z^3$: leaving groups advantageous for the pyridine synthesis reaction, and Ts: a p-toluenesulfonyl group.)

That is, when a 3-acyl-2-halopyridine derivative (7) is used as the starting material, the starting compound (IV) can be produced by employing a common N-alkylation reaction, which will be described later, in which the above derivative is allowed to react with an $R^1$-substituted amine (8), subsequently removing the protective group as occasion demands. It is possible to apply to the first production method without removing the protective group. Also, when a 3-acyl-2-(p-toluenesulfonyloxy)pyridine derivative (13) is used as the starting material, the starting compound (IV) can be produced by employing a common N-alkylation reaction, which will be described later, in which the above derivative is allowed to react with the $R^1$-substituted amine (8) in the same manner as described above. In addition, when a 2-substituted aminopyridinecarbonitrile (14) is used as the starting material, the starting compound (IV) can be produced by employing a general method for the synthesis of ketones from nitrile in which the starting material (14) is allowed to react with a Grignard's reagent (2) derived from the halide of $R^5$.

In this connection, the intermediate (7) can be produced by employing a method in which the corresponding nitrile (1) or carbonic acid (3) is used as the starting material and allowed to react with the aforementioned Grignard's reagent (2), or by oxidizing, in the general method, a 2-halo-3-substituted hydroxymethylpyridine derivative (6) which is obtained by allowing the aldehyde (5) of $R^5$ to react with a 2-halopyridine derivative (4) having high reactivity at the 3-position.

The intermediate compound (13) is obtained by reacting a ketone (9) (e.g., 1,1-diethoxypentanone) with an acylacetamide (10) and reacting 4the resulting 2-oxopyridylketone with a tosyl halide.

Production of these starting compounds can be carried its out by optionally selecting appropriate methods depending on the difference in substituents such as $R^2$, $R^3$, $R^4$ of the compound of interest. Also, a substituent may be introduced at an optional step, for example, by nitration or the like.

Second production method (mutual conversion of substituents)

The compound of the present invention can be derived from other substituent-containing compound of the present invention. The mutual substituent conversion method can be effected by employing general methods. The following describes its typical examples.

(a) Thionation

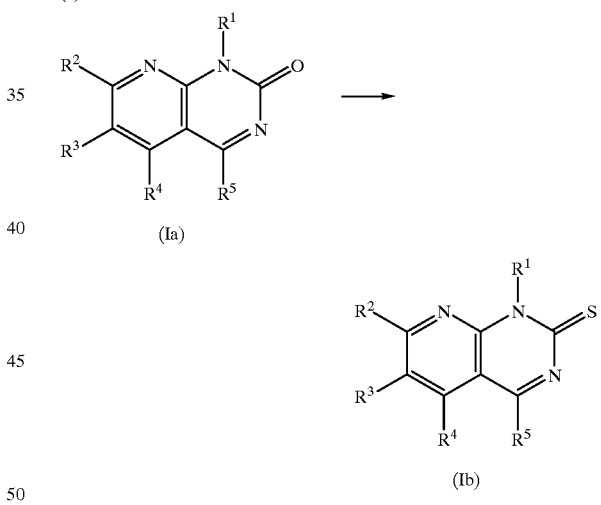

(In the above formulae, $R^1$, $R^2$, $R^3$, $R^4$ and $R^5$ are as defined in the foregoing.)

Among the compounds of the present invention, a compound (Ib) in which X is a sulfur atom can be obtained by allowing another compound (Ia) of the present invention, in which X is an oxygen atom, to react with phosphorus pentasulfide or the Lawesson reagent.

This reaction can be carried out in an organic solvent inert to the reaction such as benzene, toluene, tetrahydrofuran, ether, dioxane, methylene chloride, using the compound (Ia) and phosphorus pentasulfide or the Lawesson reagent in equivalent molar amounts, or either one in an excess amount, at room temperature or with heating as occasion demands.

(b) Reduction

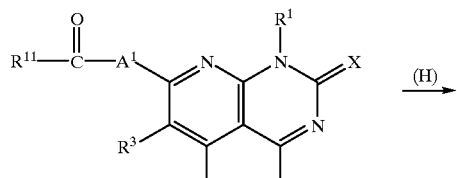

(Ic)

↓ (H)

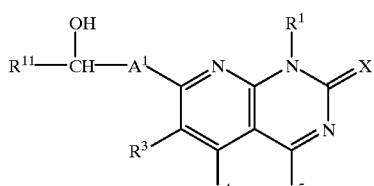

(Id)

(In the above formulae, $R^1$, $R^3$, $R^4$, $R^5$ and X are as defined in the foregoing, $R^{11}$ represents a hydrogen atom or a $C_{1-5}$ alkyl group and $A^1$ represent a single bond or a $C_{1-5}$ alkylene group.)

A hydroxy-lower alkyl compound (Id) can be produced by reducing its corresponding carbonyl compound (Ic).

The reduction is carried out by employing a general reduction method in which an alcohol compound is synthesized from a carbonyl compound. It is advantageous to carry out the reduction using sodium borohydride in a protic solvent such as ethanol or the like or by treating it with a metal hydride (e.g., lithium aluminum hydride or the like) in an inert solvent such as ether, tetrahydrofuran or the like usually under cooling condition.

(c) C-Alkylation

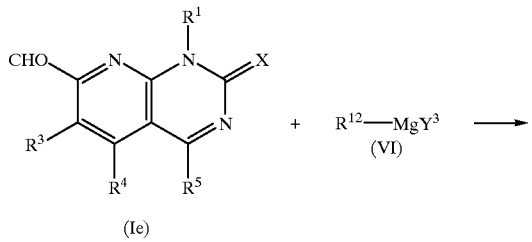

(Ie) + $R^{12}$—Mg$Y^3$ (VI) →

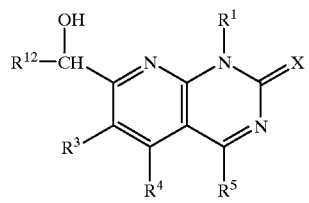

(If)

(In the above formulae, $R^1$, $R^3$, $R^4$, $R^5$, X and $Y^3$ are as defined the foregoing, and $R^{12}$ represents a $C_{1-5}$ alkyl group.)

A 2-(1-hydroxy-lower alkyl)-substituted compound (If) can be produced by a general method in which its corresponding aldehyde is allowed to react with a Grignard's reagent (VI) derived from a lower alkyl halide and magnesium.

It is advantageous to carry out the reaction in an inert solvent such as tetrahydrofuran, ether or the like, generally under cooling condition.

(d) Oxidation

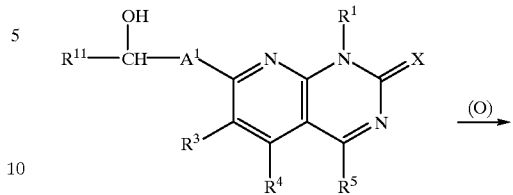

(Id)

↓ (O)

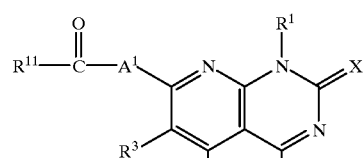

(Ic)

(In the above formulae, $R^1$, $R^3$, $R^4$, $R^5$, $R^{11}$ and $A^1$ are as defined in the foregoing.)

Contrary to the method (b), oxidation of a hydroxyl compound (Id) results in its corresponding carbonyl compound (Ic).

The oxidation is effected by employing a general method in which a carbonyl compound is produced by oxidizing its corresponding hydroxyl compound, which is generally carried out by heating the material and an oxidizing agent under reflux in an inert solvent such as benzene, toluene or the like. As the oxidizing agent, manganese dioxide, pyridinium chlorochromate or the like is advantageously used.

(e) Halogenation
 i) Halogenation of side chain (1)

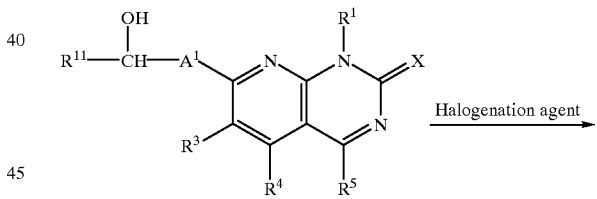

(Id)

Halogenation agent →

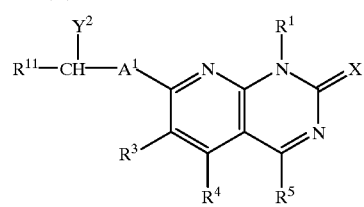

(Ig)

(In the above formulae, $R^1$, $R^3$, $R^5$, X, $R^{11}$, $Y^2$ and $A^1$ are as defined in the foregoing.)

A halogeno-lower alkyl compound (Ig) is produced by treating its corresponding hydroxyl compound (Id) with an appropriate halogenation agent in the general method. It is advantageous to carry out the reaction in a solvent inert to the reaction such as benzene, carbon tetrachloride or the like, or in the absence of solvent, using a halogenation agent such as thionyl chloride, phosphorus oxychloride, phosphorus trichloride, phosphorus pentachloride, hydrochloric acid, hydrobromic acid or the like, if necessary by heating under reflux.

ii) Halogenation of side chain (2)

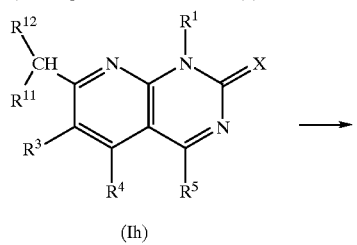

(Ih)

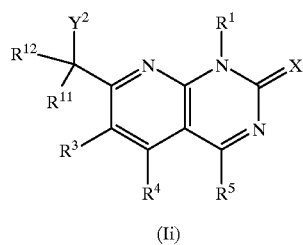

(Ii)

(In the above formulae, $R^1$, $R^2$, $R^3$ $R^4$, $R^5$, $R^{11}$ and $Y^2$ are as defined in the foregoing, and $R^{12}$ represents a hydrogen atom or a $C_{1-5}$ alkyl group which may have a substituent.)

A halogeno-lower alkyl compound (Ii) is produced by treating its corresponding alkyl compound (Ih) with an appropriate halogenation agent.

It is advantageous to carry out the reaction in a solvent inert to the reaction such as carbon tetrachloride or the like using a halogenation agent such as chlorine gas, bromine, N-bromosuccinimide or the like and heating the mixture under reflux, if necessary, in the presence of a catalyst such as 2,2'-azobisisobutyronitrile, benzoyl peroxide or the like. When N-bromosccinimide is used, the reaction can also be carried out under light irradiation in the presence of a catalyst such as 2,2'-azobisisobutyronitrile, benzoyl peroxide or the like.

iii) Halogenation of ring

It is advantageous to carry out ring halogenation at the stage of starting compound. The method described in Reference Example can be used advantageously, in which phosphorus oxychloride, phosphorus trichloride, phosphorus pentachloride, bromine or the like is used.

(f) Acylation

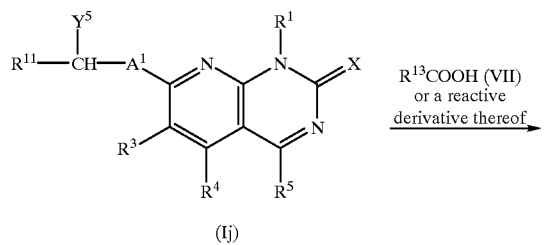

(Ij)

$R^{13}COOH$ (VII) or a reactive derivative thereof

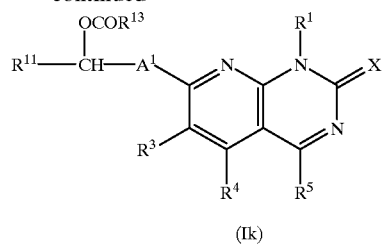

(Ik)

(In the above formulae, $R^1$, $R^3$, $R^4$, $R^5$, X, $R^{11}$ and $A^1$ are as defined in the foregoing, $Y^5$ represents a halogen atom or a hydroxyl group and $R^{13}$ represents a $C_{1-5}$ alkanoyl group.)

A lower alkanoyloxy-lower alkyl compound (Ik) can be synthesized easily by an esterification method in which its corresponding carboxylic acid (VII) or a reactive derivative thereof such as ester, acid anhydride or the like is allowed to react with a corresponding hydroxyl compound or halide (Ij). Common esterification method can be applied to this reaction.

In this connection, a lower alkanoylthio-lower alkyl compound can also be produced by similar esterification method. In addition, the lower alkanoyloxy-lower alkyl compound can also be obtained by a method in which its corresponding halogeno-lower alkyl compound is allowed to react with an alkali metal salt of corresponding carboxylic acid.

(g) Saponification

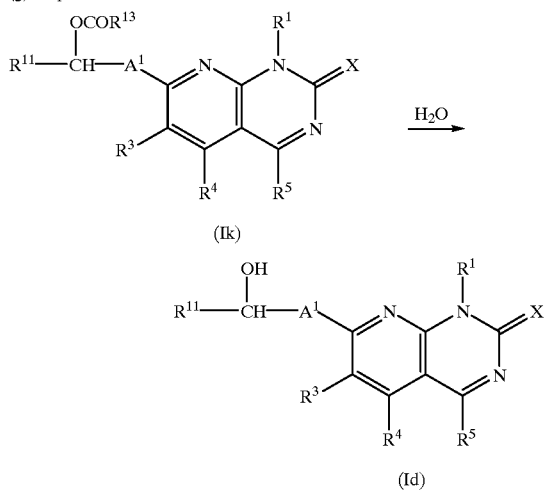

(In the above formulae, $R^1$, $R^3$, $R^4$, $R^5$, X, $R^{11}$, $R^{13}$ and $A^1$ are as defined in the foregoing.)

Contrary to the production method (f), corresponding hydroxyl compound (Id) can be synthesized using an ester compound (Ik) as the raw material. It can be produced by a commonly used method in which the starting material is treated with a base such as sodium hydroxide or the like.

(h) Oxime Formation

The compound of the present invention having a hydroxylimino group or a lower alkoxyimino group can be produced by reacting the corresponding aldehyde or ketone compound with hydroxylamine or a lower alkoxyamine.

The reaction may be carried out by employing a general method, for example, by reacting the aldehyde or ketone compound and hydroxylamine or a lower alkoxyamine or a salt thereof in equivalent molar mounts or either one in a slightly excess amount, in an organic solvent inert to the reaction (e.g., methanol and ethanol) and, if desired, in the presence of a base (e.g., sodium carbonate and sodium acetate) under cooling, under room temperature, or under refluxing temperature.

Third production method (N-Alkylation)

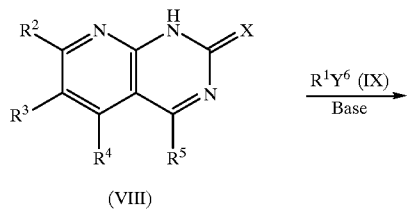

(VIII)

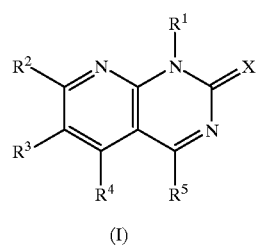

(I)

(In the above formulae, $R^1$, $R^2$, $R^3$, $R^4$, $R^5$, and X are as defined in the foregoing, and $Y^6$ represents a leaving group which is advantageous for this reaction.)

In this production method, the compound (I) of the present invention is produced by allowing a compound (VIII) to react with a compound (IX).

Illustrative examples of the leaving group represented by $Y^6$ include halogen atoms such as iodine, bromine, chlorine and the like, and organic sulfonic acid residues such as alkyl sulfonyloxy groups (e.g., methanesulfonyloxy, ethanesulfonyloxy and the like) and aryl sulfonyloxy groups (e.g., benzenesulfonyloxy, toluene(particularly p-toluene) sulfonyloxy, and the like).

This reaction is carried out using the compound (VIII) and the compound (IX) in equivalent molar amounts, or either one in an excess amount, in an organic solvent inert to the reaction such as benzene, toluene, diethyl ether, tetrahydrofuran, dioxane dimethylformamide, dimethyl sulfoxide or the like, in the presence of a base, and at cooling temperature of −78° C. to 0° C., at room temperature or, as occasion demands, with heating. Illustrative examples of the base to be used include sodium hydride, potassium hydride, lithium diisopropylamide, lithium hexamethyldisilazide, tert-butoxy potassium, sodium methoxide and the like. This reaction can also be carried out using a base such as sodium alcholate, potassium alcholate, sodium hydroxide, potassium hydroxide or the like in an alcoholic solvent such as methanol, etharol or the like.

In this connection, the starting compound (VIII) can be subjected to the reaction without using a base, when its 1-position is substituted with an alkali metal.

The thus produced compound of the present invention is isolated and purified in a free form or as a salt thereof by subjecting it to a commonly used salt formation reaction. Isolation and purification are carried out by employing usual chemical treatments such as extraction, concentration, evaporation, crystallization, filtration, recrystallization, and various types of chromatography.

Various types of isomers can be isolated in the usual way making use of differences in physicochemical properties among isomers. For example, a racemic compound can be introduced into stereochemically pure isomers by a general racemic resolution method (e.g., a method in which optical resolution is effected by introducing into a diastereomer salt with a general optically active acid such as tartaric acid). Also, a diastereomer mixture can be separated by commonly used means such as a fractional crystallization, a chromatography or the like.

In addition, an optically active compound can be produced by using an appropriate optically active material.

Industrial Applicability

The compounds of the present invention represented by the general formula (I) or pharmaceutically acceptable salts thereof are useful as medicines, because they have an excellent activity to inhibit type IV PDE, and the activity is selective for type IV PDE.

In consequence, the compounds of the present invention can be used for the prevention or treatment of various diseases in which type IV PDE is concerned. The following exemplifies such a type of diseases.

Respiratory diseases [e.g., bronchial asthma (including atopic asthma), chronic bronchitis, pneumonia, adult respiratory distress syndrome (ARDS) and the like], inflammatory diseases [e.g., atopic dermatitis, conjunctivitis, urticaria, acquired immunodeficiency syndrome (AIDS), keloid formation, rhinitis, iridocylitis, gingivitis, periodontitis, alveolar pyorrhea, gastritis, ulcerative colitis, Crohn disease, gastrointestinal ulcer, esophagitis, myositis, encephalitis (myasthenia gravis, multiple sclerosis and neuritis), hepatitis, cicatrization, nephritis (including proliferative nephritis), peritonitis, pleuritis, scleritis, scleroderma, burn injury and the like], a systemic or local arthropathy (e.g., osteoarthrosis, gouty arthritis, chronic rheumatoid arthritis, malignant rheumatoid, psoriatic arthritis and the like), proliferative diseases [e.g., malignant tumor, leukemia, proliferative dermatopathy (keratosis and various types of dermatitis), collagen disease and the like], diseases related to nervous function abnormality (e.g., learning, memory and cognition disturbances related to nervous degeneration diseases such as Alzheimer disease, Parkinson disease and the like, multiple lateral sclerosis, senile dementia, amyotrophic lateral sclerosis, acute demyelinating neuritis, muscular dystrophy and the like), diseases with mental function abnormality (e.g., manic-depressive psychosis, schizoid, anxiety, panic and the like), inflammation due to organ transplantation and the like (e.g., reperfusion injury, graft versus host reaction and the like), diseases which require protection of nerves and cells [e.g., cardiac arrest, spinal cord injury, intermittent claudication, ischemic diseases (e.g., angina pectoris, myocardial infarction, stroke, head injury and the like) and the like], diseases related to micturition (e.g., diabetes insipidus, urethritis, urinary incontinence, cystitis, irritable bladder, neurogenic bladder, uremia, tubular disorder, pollakiuria, urinary retention and the like), endocrine diseases including diabetes mellitus (e.g., diabetic retinopathy, diabetic nephropathy, diabetic neuropathy, amyloidosis, pancreatitis, thyroiditis, obesity, prostatic hypertrophy and the like), diseases in which tumor necrosis factor (TNF) and other cytokine (IL-1, IL-6 and the like) are concerned [e.g., psoriasis, rheumatoid arthritis, ulcerative colitis, Crohn disease, sepsis, septic shock, endotoxin shock, Gram negative bacillus sepsis, toxic shock syndrome, nephritis, hepatitis, infection (bacterial and viral), circulatory failure (heart failure, arteriosclerosis, myocardial infarction, stroke) and the like], autoimmune diseases (e.g., systemic lupus erythematosus, atrophic gastritis, thyroid gland disease, glomerulonephritis, orchitis, adrenal disease, hemolytic anemia, oophoritis and the like), circulatory organ diseases (e.g., hypertension, angina pectoris, heart failure, myocarditis, epicarditis, endocarditis, valvulitis and the like), diseases of vascular and blood systems (e.g., angitis, aneurysm, vascular endothelial injury, thrombosis inflammation, granuloma, cerebrovascular inflammation, arteriosclerosis, perivascular inflammation, leukopenia, thrombocytopenia, sarcoidosis and the like), diseases in which immune allergy reactions are concerned (e.g., contact dermatitis, serum sickness, drug allergy, Goodpasture syndrome, lymphomatosis, rheumatic fever, AIDS, anaphylactic shock and the like), and other diseases [glaucoma, spastic paralysis, impotence, diseases with pain (e.g., contusion, headache and the like), cervico-omo-branchial syndrome, nephropathy, renal insufficiency, hepatic insufficiency and obesity].

The compound (I) of the present invention is particularly useful for the prevention or treatment of respiratory diseases [e.g., bronchial asthma (including atopic asthma), chronic bronchitis, pneumonia, ARDS and the like], inflammatory diseases [e.g., atopic dermatitis, conjunctivitis, urticaria, AIDS, keloid formation, rhinitis, iridocylitis, gingivitis, periodontitis, alveolar pyorrhea, gastritis, ulcerative colitis, Crohn disease, gastrointestinal ulcer, esophagitis, myositis, encephalitis (myasthenia gravis, multiple sclerosis and neuritis), hepatitis, cicatrization, nephritis (including proliferative nephritis), peritonitis, pleuritis, scleritis, scleroderma, burn injury and the like], and diseases in which tumor necrosis factor (TNF) and other cytokine (IL-1, IL-6 and the like) are concerned [e.g., psoriasis, rheumatoid arthritis, ulcerative colitis, Crohn disease, sepsis, septic shock, endotoxin shock, Gram negative bacillus sepsis, toxic shock syndrome, nephritis, hepatitis, infection (bacterial and viral), circulatory failure (heart failure, arteriosclerosis, myocardial infarction, stroke) and the like].

More particularly, the compounds of the present invention are useful as excellent preventive and treating agents of respiratory diseases such as bronchial asthma and the like.

Also, since the compounds of the present invention show extremely weak vomiting action in comparison with the prior phosphodiesterase inhibitors, they are particularly useful for the treatment or prevention of diseases in patients who require systemic administration.

Activities of the compounds of the present invention to inhibit type IV and types I, II, III and V phosphodiesterase were confirmed by the following tests. Phosphodiesterase Inhibition Activity Measuring Test (in vitro)

(1) Method for Measuring Type IV Phosphodiesterase Inhibition Activity

The following assay was used for the evaluation of the capability of the compounds of the present invention to inhibit type IV phosphodiesterase.

1) Physiological saline (200 ml) supplemented with dextran (3%) was added to 500 ml of heparinized peripheral blood of a healthy person and incubated at 37° C. for 40 minutes to effect precipitation of erythrocytes. The supernatant after precipitation of erythrocytes was recovered and centrifuged once, and the resulting precipitate was suspended in buffer A (140 mM NaCl, 5 mM KCl, 5 mM glucose and 10 mM HEPES, pH 7.4), overlaid on a solution for density gradient centrifugation use (Ficoll solution) and then centrifuged at room temperature for 40 minutes at 450×g, thereby separating monocyte fraction and granulocyte fraction. The granulocyte fraction was washed once with buffer B (140 mM NaCl, 5 mM KCl; 1 mM $CaCl_2$, 1 mM $MgCl_2$, 5 mM glucose and 10 mM HEPES, pH 7.4) and suspended in buffer C (20 mM Bis-Tris, 5 mM dithioerythritol, 2 mM EGTA and 50 mM sodium acetate, pH 6.5) containing a protease inhibitor (50 $\mu$M phenylmethyl-sulfonyl-fluoride, 5 $\mu$M pepstatin A, 40 $\mu$M leupeptin, 20 $\mu$M aprotinin or 2 mM benzamidine) and then the cells were disrupted using polytron and sonicator and subjected to ultracentrifugation (4° C., 100,000×g, 60 minutes) to give a soluble fraction.

2) The thus obtained soluble fraction was applied to a column of 1.6×10 cm packed with Q Sepharose which had been equilibrated with buffer C. Next, the column was washed with 300 ml of buffer C to remove non-absorbed protein. Phosphodiesterase was eluted with 200 ml of buffer C having 0.05 to 1.25 M linear gradient of sodium acetate to collect 40 fractions each containing 5.0 ml eluate. Each fraction was checked for cAMP- and cGMP-metabolizing phosphodiesterase activities. Fractions having no cGMP- but cAMP-metabolizing activity and showing disappearance of the metabolizing activity by 10 $\mu$M rolipram (a type IV phosphodiesterase selective inhibitor) were collected to be used as a stock solution for the examination of type IV phosphodiesterase inhibition activity.

3) A predetermined amount of each compound to be tested was subjected to 10 minutes of reaction at 30° C. in a reaction mixture containing 40 mM Tris-HCl (pH 8.0), 5 mM $MgCl_2$, 4 mM 2-mercaptoethanol, 0.3 $\mu$M cilostamide (an III type phosphodiesterase selective inhibitor), 1 $\mu$M cAMP, 10 nM $^3$H-cAMP and the type IV phosphodiesterase stock solution. The reaction solution was boiled at 90° C. for 1 minute, cooled in an ice bath, mixed with 1 unit of 5'-nucleotidase and then subjected to 10 minutes of reaction at 30° C., and the reaction was stopped by the addition of 1 ml of methanol. The reaction solution was passed through a Dowex 1×8 column to adsorb un-hydrolyzed material and then the radioactivity was measured.

4) Concentration of each compound to be tested which inhibits 50% of the metabolic activity of type IV phosphodiesterase was calculated and expressed as $IC_{50}$. Test results: Results of the measurement of the activity of the compounds of the present invention to inhibit type IV PDE are shown in Tables 1 and 2, together with the results of the compounds illustratively disclosed in the aforementioned U.S. Patent and similar comparative compounds which were separately synthesized.

TABLE 1

| Compound | Type IV PDE inhibition activity $IC_{50}$ (nM) |
| --- | --- |
| Example 19 | 8.08 |
| Example 22 | 7.80 |
| Example 33 | 6.19 |
| Example 34 | 1.47 |
| Example 36 | 0.93 |
| Example 37 | 4.75 |
| Example 40 | 5.79 |

TABLE 1-continued

| Compound | Type IV PDE inhibition activity IC$_{50}$ (nM) |
| --- | --- |
| Example 41 | 0.85 |

TABLE 2

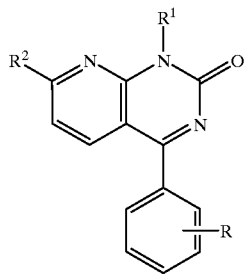

| Compounds Tested | | | Type IV PDE Inhibition |
| --- | --- | --- | --- |
| R$^1$ | R$^2$ | R | IC$_{50}$ (nM) |
| Example 1 | —CH$_2$CH$_3$ | —CH$_2$CH$_3$ | m-Cl | 0.81 |
| Example 2 | —CH$_2$CH$_3$ | —CH$_2$CH$_3$ | m-Br | 1.15 |
| Example 3 | —CH$_2$CH$_3$ | —CH$_3$ | m-Cl | 2.32 |
| Example 4 | —CH$_2$CH$_3$ | —CH$_3$ | m-Br | 1.45 |
| Example 5 | —CH$_2$CH$_3$ | —CH$_3$ | m-CH$_3$ | 3.50 |
| Example 6 | —CH$_2$CH$_3$ | —CH$_2$CH$_3$ | m-CH$_3$ | 3.70 |
| Comparative Compound 1 | —CH$_2$CH$_3$ | —H | o-Cl | 2842 |
| Comparative Compound 2 | —CH(CH$_3$)$_2$ | —H | p-Cl | >3000 |
| Comparative Compound 3 | —CH$_2$CH$_3$ | —H | p-Cl | >3000 |
| Comparative Compound 4 | —CH(CH$_3$)$_2$ | —H | m,p-diCl | >3000 |
| Comparative Compound 5 | —CH$_2$CH$_3$ | —H | m,p-diCl | >3000 |
| Comparative Compound 6 | —CH(CH$_3$)$_2$ | —H | m-Cl | 803 |
| Comparative Compound 7 | —CH$_2$CH$_3$ | —H | m-Cl | 308 |
| Comparative Compound 8 | —CH$_2$CH$_3$ | —H | m—CH$_3$ | 612 |

Comparative compound 1: 4-(2-chlorophenyl)-1-ethylpyrido[2,3-d]pyrimidin-2(1H)-one; mp., 134–135° C. (AcOEt-hexane)
Comparative compound 2: compound of Example 5f in the aforementioned U.S. Patent
Comparative compound 3: 4-(4-chlorophenyl)-1-ethylpyrido[2,3-d]pyrimidin-2(1H)-one; mp., 221–222° C. (AcOEt-hexane)
Comparative compound 4: compound of Example 5e in the aforementioned U.S. Patent
Comparative compound 5: 4-(3,-4-dichlorophenyl)-1-ethylpyrido[2,3-d]pyrimidin-2(1H)-one; mp., 236–239° C. (AcOEt-iPr$_2$O)
Comparative compound 6: 4-(3-chlorophenyl)-1-isopropylpyrido[2,3-d]pyrimidin-2(1H)-one; mp., 169–171° C. (AcOEt-iPr$_2$O)
Comparative compound 7: 4-(3-chlorophenyl)-1-ethylpyrido[2,3-d]pyrimidin-2(1H)-one; mp., 154–156° C. (AcOEt-hexane)
Comparative compound 8: 4-(3-methylphenyl)-1-ethylpyrido[2,3-d]pyrimidin-2(1H)-one; mp., 148–149° C. (AcOEt-hexane)

As is evident from the above test results, compounds of the present invention are possessed of markedly high activity to inhibit type IV PDE.

Particularly, in compounds of 4-(substituted phenyl)-1-substituted pyrido[2, 3-d]pyrimidin-2(1H)-one type compounds having the substituent of 4-position phenyl group on the ortho or para position have extremely low type IV PDE inhibition activity. The same can be said of compounds which are di-substituted at para and meta positions. On the contrary, compounds having the substituent only on the meta position (comparative compounds) have one order-higher activity than those having ortho-, para- or di-substituted compounds. In addition, compounds of the present invention in which the 4-position phenyl group has a substituent only on its meta position and a lower alkyl group is introduced into the 7-position is markedly excellent in the type IV PDE inhibition activity in comparison with compounds having a substituent only on the meta position.

In consequence, among compounds of 4-(substituted phenyl)-1-substituted pyrido[2,3-d]pyrimidin-2(1H)-one type compounds of the present invention in which the 4-position phenyl group has a substituent only on its meta position and a lower alkyl-based substituent is introduced into the 7-position, particularly the compounds shown in Table 2 [included in the compound (II) of the present invention], have a markedly excellent activity to inhibit type IV PDE, even in comparison with the inherent effect of the compounds illustratively described in the aforementioned U.S. Patent.

(2) Method for measuring the activity to inhibit various phosphodiesterase isozymes

[A] In order to evaluate selectivity of the compounds of the present invention for type IV phosphodiesterase, I, II, III and V type phosphodiesterase isozymes were purified in the following manner.

1) Solutions containing various phosphodiesterase (I, II and III types) isozymes were purified from rat heart muscle cells in the following manner. Under ether anesthesia, Wistar rat was subjected to thoracotomy to excise the heart. After removing blood by perfusion with physiological saline supplemented with heparin (1 unit/ml), the heart was finely chopped with scissors. This was suspended in buffer A (20 mM Bis-Tris, 5 mM dithioerythritol, 2 mM EGTA and 50 mM sodium acetate, pH 6.5) containing a protease inhibitor (50 $\mu$M phenyl-methyl-sulfonyl-fluoride, 5 $\mu$M pepstatin A, 40 $\mu$M leupeptin, 20 $\mu$M aprotinin or 2 mM benzamidine) and then the cells were disrupted using polytron and sonicator and subjected to ultracentrifugation (4° C., 100,000×g, 60 minutes) to give a soluble fraction.

2) Solutions containing various phosphodiesterase isozymes were obtained from the thus obtained soluble fraction in the following manner. The thus obtained soluble fraction was applied to a column of 1.6×10.0 cm packed with Q Sepharose which had been equilibrated with buffer A. Next, said column was washed with 300 ml of buffer A to remove non-absorbed protein. Phosphodiesterase was eluted with 200 ml of buffer A having 0.05 to 1.25 M linear gradient of sodium acetate to collect about 40 fractions each containing 5.0 ml eluate. Each fraction was checked for cAMP- and cGMP-metabolizing phosphodiesterase activities. Of these fractions, a fraction having only cAMP-metabolizing activity and showing disappearance of the metabolizing activity by 0.1 $\mu$M cilostamide (an III type phosphodiesterase selective inhibitor) was used as the III type phosphodiesterase. Also, a fraction which showed increased cAMP metabolizing activity by the addition of 2 $\mu$M cGMP was used as the II type phosphodiesterase. In addition, a fraction which did not show changes in the cAMP metabolizing activity by the addition of cGMP but the cAMP metabolizing activity was increased by the addition of 2 mM CaCl$_2$ was used as the I type phosphodiesterase. These fractions were separately collected to be used as phosphodiesterase (types I, II and III) stock solutions for the examination of selectivity.

3) A solution containing type V phosphodiesterase was prepared from peripheral blood of a healthy person in the following manner. A 200 ml portion of physiological saline supplemented with dextran (3%) was added to 500 ml of heparinized peripheral blood and incubated at 37° C. for 40 minutes to effect precipitation of erythrocytes. The supernatant fluid after precipitation of erythrocytes was recovered and centrifuged once, and the resulting precipitate was suspended in buffer B (140 mM NaCl, 5 mM KCl, 5 mM glucose and 10 mM HEPES, pH 7.4), overlaid on a solution for density gradient centrifugation use (Ficoll solution) and then centrifuged at room temperature for 40 minutes at 450×g, thereby separating monocyte fraction and granulocyte fraction. The granulocyte fraction was washed once with buffer C (140 mM NaCl, 5 mM KCl, 1 mM CaCl$_2$, 1 mM MgCl$_2$, 5 mM glucose and 10 mM HEPES, pH 7.4) and suspended in buffer D (20 mM Bis-Tris, 5 mM dithioerythritol, 2 mM EGTA and 50 mM sodium acetate, pH 6.5) containing a protease inhibitor (40 $\mu$M leupeptin, 5 $\mu$M pepstatin A 20 $\mu$M aprotinin, 50 $\mu$M phenyl-methyl-sulfonyl-fluoride or 2 mM benzamidine) and then the cells were disrupted using polytron and sonicator and subjected to ultracentrifugation (4° C., 100,000×g, 60 minutes) to give a soluble fraction.

4) The thus obtained soluble fraction was applied to a column of 1.6×10 cm packed with Q Sepharose which had been equilibrated with buffer D. Next, the column was washed with 120 ml of buffer D to remove non-absorbed protein. Phosphodiesterase was eluted with 300 ml of buffer D having 0.05 to 1.25 M linear gradient of sodium acetate to collect fractions each containing 5.0 ml eluate. Each fraction was checked for cAMP- and cGMP-metabolizing phosphodiesterase activities. Fractions having only cGMP metabolizing activity were collected to be used as the type V phosphodiesterase stock solution.

[B] Inhibitory activities were measured using the thus obtained stock solutions of various phosphodiesterase isozymes.

1) A predetermined amount of each compound to be tested was subjected to 10 minutes of reaction at 30° C. in a reaction mixture containing 40 mM Tris-HCl (pH 8.0), 5 mM MgCl$_2$, 4 mM 2-mercaptoethanoly 10 $\mu$M rolipram (an type IV phosphodiesterase selective inhibitor), 1 $\mu$M cAMP, 10 nM $^3$H-cAMP (in the case of type V phosphodiesterase, 1 $\mu$M cAMP and 10 nM $^3$H-cAMP are replaced by 1 $\mu$M cGMP and 100 nM $^3$H-cGMP) and each of the isozyme stock-solutions. After completion of the reaction, the reaction mixture was boiled at 90° C. for 1 minute, cooled in an ice bath, mixed with 1 unit of 5'-nucleotidase and then subjected to 10 minutes of reaction at 30° C., and the reaction was stopped by adding 1 ml of methanol. The reaction solution was passed through a Dowex 1×8 column to effect adsorption of un-metabolized cAMP or cGMP and then radioactivity in the eluate was measured using a scintillation counter.

20 2) The IC$_{50}$ value of each compound to be tested was calculated as a concentration of the compound which inhibits 50% of the metabolic activity of each of the isozymes, and selectivity of the inhibition activity (IC$_{50}$) was evaluated. Test results: Results of the above measurement confirmed that most of the compounds of the present invention are excellent in selectively inhibiting type IV PDE activity in comparison with other PDE isozymes.

For example, with respect to the compounds of Examples 1, 3, 4, and 19, it was confirmed that the selectivity in inhibition activity against type IV PDE was 1000 times or more higher than that against the other types of PDE.

(3) Inhibition of Antigen-Induced Airway Inflammatory Cell Infiltration

1) Male Hartley guinea pigs of were used after their active sensitization by peritoneal cavity treatment (three times at one week interval) with egg albumin (5 $\mu$g) and aluminum hydroxide gel (100 mg). The airway inflammation was induced by 30 minutes of inhalation exposure to 0.5% egg albumin under intravenous treatment with an H$_1$-histamine antagonist, pyrilamine (2 mg/kg).

2) Each compound to be tested was suspended in purified water containing 0.5% methylcellulose and administered orally 30 minutes before or 3 hours after the egg albumin exposure. In the control group, solvent (0.5% methylcellulose purified water, 3 ml/kg) was administered in the same manner. After 24 hours of the egg albumin exposure, the animals were sacrificed by releasing blood from the abdominal aorta under anesthesia with urethane (2 g/kg, intraperitoneal injection) and subjected to alveolus washing with physiological saline (10 ml×3 times).

3) Total number of white blood cells in the alveorus washing solution were counted using a blood cell counter (Celltac-$\alpha$, Nippon Koden). Also, the ratio of respective white blood cells (eosinophil, moonocyte, lymphocyte and neutrophil) was obtained by microscopically observing white blood cells in the alveorus washing solution, which have been smeared on a slide glass and stained with DifQuick (The Green Cross Corporation), and the airway infiltration number of respective white blood cells was calculated based on the following formula.

[The number of respective white blood cells (eosinophil, monocyte, lymphocyte and neutrophil)]=[total white blood cell count]×[ratio of respective white blood cells (eosinophil, monocyte, lymphocyte and neutrophil)]

4) The ED$_{50}$ value was calculated from the inhibition ratio of total infiltration white blood cell count at each dose of each compound to be tested based on the count in the control group. In addition, inhibition action upon the number of respective white blood cells (eosinophil, monocyte, lymphocyte and neutrophil) was judged by the significant difference ($p<0.05$) of Dunnett's test. Test results: Results of the above measurement confirmed that compounds of the present invention have excellent action in inhibiting infiltration of airway inflammatory cells and therefore are expected to be used as an excellent bronchial asthma-treating agent.

A pharmaceutical preparation which contains one or a plurality of the compounds of the present invention or salts thereof as the active ingredient is prepared using carriers, excipients and other additive agents generally used in the preparation of medicines.

It can be administered by oral administration in the dosage form of tablets, pills, capsules, granules, powders, solutions and the like or by parenteral administration in the form of injections (e.g., intravenous injection, intramuscular injection, and the like), suppositories, transdermal preparations, inhalants and the like or by intravesical injection. Its dose is optionally decided case by case taking symptoms, age, sex and the like of each patient into consideration, and it may be generally from about 0.001 mg/kg to about 100 mg/kg per day per adult in the case of oral administration, and the daily dose may be used once a day or divided into 2 to 4 doses per day. When administered by intravenous injection due to the symptoms, it may be administered once a day or a plurality of doses a day within the range of from 0.001 mg/kg to 10 mg/kg per adult. Also, in the case of inhalation, it may be administered once a day or a plurality of doses a day generally within the range of from 0.0001 mg/kg to 1 mg/kg per adult, or, in the case of application, it may be administered once a day or a plurality of doses a day generally within the range of from 0.0001 mg/kg to 1 mg/kg per adult.

Tablets, powders, granules and the like are used as the solid composition of the present invention for oral administration use. In such a solid composition, one or more of the active substances are mixed with at least one inert diluent such as lactose, mannitol, glucose, hydroxypropylcellulose, microcrystalline cellulose, starch, polyvinyl pyrrolidone or aluminum magnesium silicate. In accordance with the usual way, the composition may further contain additive agents other than the inert diluent, such as lubricants (e.g., magnesium stearate or the like), disintegrators (e.g., calcium cellulose glycolate or the like), stabilizers (e.g., lactose or the like) and solubilizing agents (e.g., glutamic acid, aspartic acid or the like). As occasion demands, tablets or pills may be coated with sugar or films of a gastric or enteric substance such as sucrose, gelatin, hydroxypropylcellulose or hydroxypropylmethylcellulose phthalate.

The liquid composition for oral administration use includes pharmaceutically acceptable emulsions, solutions, suspensions, syrups, elixirs and the like, and contains generally used inert diluent such as purified water or ethanol. In addition to the inert diluent, this composition may also contain auxiliary agents such as moistening agents, suspending agents and the like, sweeteners, flavors, aromatics and antiseptics.

The injections for parenteral administration use include aseptic aqueous or non-aqueous solutions, suspensions and emulsions. Distilled water for injection use, physiological saline and the like are used in the aqueous solutions and suspensions. Propylene glycol, polyethylene glycol, plant oils (e.g., olive oil), alcohols (e.g., ethanol), polysorbate 80 and the like are used in the non-taqueous solutions and suspensions. These compositions may also contain auxiliary agents such as antiseptics, moistening agents, emulsifying agents, dispersing agents, stabilizing agents (e.g., lactose) and solubilizing agents (e.g., glutamic acid and aspartic acid). These compositions are sterilized, for example, by filtration through a bacteria retaining filter, blending of a germicide or irradiation. Also, these compositions may be produced as aseptic solid compositions which are used by dissolving in sterile water or a sterile solvent for injection use prior to their use.

BEST MODE OF CARRYING OUT THE INVENTION

The following describes the present invention further in detail with reference to examples. As a matter of course, the present invention should not be limited to the description of Examples.

Starting compounds of the present invention include novel compounds. Production methods of the starting compounds are shown in Reference Examples.

REFERENCE EXAMPLE 1

A mixture of 3-cyano-6-ethyl-2(1H)-pyridone (36.2 g, 0.24 mol) and phosphorus oxychloride (250 ml) was heated under reflux for 2 hours. The reaction solution was concentrated under a reduced pressure, and the resulting residue was mixed with toluene and concentrated under a reduced pressure. The thus obtained residue was diluted with chloroform and washed with 1 N sodium hydroxide aqueous solution. The aqueous layer was extracted with chloroform, and the chloroform layers were combined and dried over anhydrous magnesium sulfate. After removing magnesium sulfate by filtration, the filtrate was concentrated under a reduced pressure and the resulting residue was purified by silica gel column chromatography (hexane-ethyl acetate) to give 2-chloro-3-cyano-6-ethylpyridine (19.6 g, 49%) as an oily material.

REFERENCE EXAMPLE 2

Magnesium (2.72 g, 112 mmol) was added to a tetrahydrofuran (200 ml) solution of 3-bromochlorobenzene (22.1 g, 115 mmol), and the mixture was stirred at room temperature. Since spontaneous exothermic reaction occurred, the stirring was continued until the exothermicity was ceased. The reaction solution was cooled to −20° C., mixed with 2-chloro-3-cyano-6-ethylpyridine (9.33 g, 56 mmol) and then stirred for 16 hours at room temperature. The reaction solution was mixed with saturated ammonium chloride aqueous solution and stirred for 30 minutes at room temperature and then mixed with 1 N hydrochloric acid and extracted with ethyl acetate. The organic layer was dried over anhydrous magnesium sulfate, magnesium-sulfate was removed by filtration and then the filtrate was concentrated under a reduced pressure. Thereafter, the resulting residue was purified by silica gel column chromatography (hexane-ethyl acetate) to give 2-chloro-3-(3-chlorobenzoyl)-6-ethylpyridine (3.48 g, 22%) as a pale yellow oily material.

REFERENCE EXAMPLE 3

The following compound was obtained in the same manner as described in Reference Example 2.
3-(3-Bromobenzoyl)-2-chloro-6-ethylpyridine

REFERENCE EXAMPLE 4

Magnesium (4.8 g, 200 mmol) was added to a tetrahydrofuran (400 ml) solution of 3-bromochlorobenzene (38 g, 200 mmol), and the mixture was stirred at room temperature. Since spontaneous exothermic reaction occurred, the stirring was continued until the exothermicity was ceased. The reaction solution was cooled to −40° C., mixed with 2-chloro-6-methylnicotinic acid (9.2 g, 53 mmol) and then stirred overnight at room-temperature. The reaction solution was mixed with saturated ammonium chloride aqueous solution and extracted with ethyl acetate. The organic layer was dried over anhydrous magnesium sulfate, magnesium sulfate was removed by filtration and then the filtrate was concentrated under a reduced pressure. Thereafter, the resulting residue was purified by silica gel column chromatography (chloroform) to give 2-chloro-3-(3-chlorobenzoyl)-6-methylpyridine (6.25 g, 44%) as an oily material.

REFERENCE EXAMPLE 5

The following compound was obtained in the same manner as described in Reference Example 4.
3-(Bromobenzoyl)-2-chloto-6-methylpyridine

REFERENCE EXAMPLE 6

A mixture of 2-chloro-3-(3-chlorobenzoyl)-6-ethylpyridine (3.4 g, 12 mmol) and 70% ethylamine aqueous solution (15 ml) was sealed in a tube and stirred at 100° C. for 4 hours. The reaction solution was cooled to room temperature and then transferred into a separating funnel. This was acidified by adding 1 N hydrochloric acid, vigorously shaken and then alkalified by adding 1 N sodium hydroxide aqueous solution. This was extracted with chloroform, the resulting organic layer was dried over anhydrous magnesium sulfate, magnesium sulfate was removed by filtration and then the filtrate was concentrated under a reduced pressure. Thereafter, the resulting residue was purified by silica gel column chromatography (hexane-ethyl acetate) to give 3-(3-chlorobenzoyl)-6-ethyl-2-ethylaminopyridine (2.6 g, 76%) as a yellow oily material.

The following compounds of Reference Examples 7 to 9 were obtained in the same manner as described in Reference Example 6.

REFERENCE EXAMPLE 7
3-(3-Bromobenzoyl)-6-ethyl-2-ethylaminopyridine

REFERENCE EXAMPLE 8
3-(3-Chlorobenzoyl)-2-ethylamino-6-methylpyridine

REFERENCE EXAMPLE 9
3-(3-Bromobenzoyl)-2-ethylamino-6-methylpyridine

REFERENCE EXAMPLE 10

Magnesium (4.82 g, 200 mmol) was added to a tetrahydrofuran (300 ml) solution of 3-bromotoluene (35.1 g, 200 mmol), and the mixture was stirred at room temperature. Since spontaneous exothermic reaction occurred, the stirring was continued until the exothermicity was ceased. The reaction solution was cooled to −40° C., mixed with 2-chloro-6-methylnicotinic acid (11.6 g, 68 mmol) and then stirred for 16 hours at room temperature. The reaction solution was mixed with saturated ammonium chloride aqueous solution and extracted with ethyl acetate. The organic layer was dried over anhydrous magnesium sulfate, magnesium sulfate was removed by filtration and then the filtrate was concentrated under a reduced pressure. Thereafter, the resulting residue was purified by silica gel column chromatography (hexane-ethyl acetate) to give 2-chloro-6-methyl-3-(3-methylbenzoyl)pyridine (8.70 g, 52%) as a pale yellow oily material.

REFERENCE EXAMPLE 11

3-Bromotoluene (12.5 g, 73.1 mmol) was added to a tetrahydrofuran (200 ml) solution of magnesium (1.70 g, 70.0 mmol), and the mixture was stirred until magnesium pieces disappeared. The reaction solution was cooled to −20° C., mixed with 2-chloro-3-cyano-6-ethylpyridine (10.6 g, 63.6 mmol) and then stirred for 17 hours at room temperature. The reaction solution was mixed with saturated ammonium chloride aqueous solution and 1 N hydrochloric acid, and the mixture was stirred for 2 hours at room temperature and then extracted with ethyl acetate. The organic layer was dried over anhydrous magnesium sulfate, magnesium sulfate was removed by filtration and then the filtrate was concentrated under a reduced pressure. Thereafter, the resulting residue was purified by silica gel column chromatography (hexane-ethyl acetate) to give 2-chloro-6-ethyl-3-(3-methylbenzoyl)pyridine (9.19 g, 56%) as a yellow oily material.

REFERENCE EXAMPLE 12

A mixture of 2-chloro-6-methyl-3-(3-methylbenzoyl) pyridine (2.45 g, 10 mmol) and 70% ethylamine aqueous solution (10 ml) was sealed in a tube and stirred for 4 hours at 100° C. The reaction solution was cooled to room temperature and transferred into a separating funnel. This was adjusted to pH 1 with 1 N hydrochloric acid, vigorously shaken, adjusted to pH 10 by adding 1 N sodium hydroxide aqueous solution and then extracted with chloroform. The organic layer was dried over anhydrous magnesium sulfate, magnesium sulfate was removed by filtration and then the filtrate was concentrated under a reduced pressure. Thereafter, the resulting residue was purified by silica gel column chromatography (hexane-ethyl acetate) to give 2-ethylamino-6-methyl-3-(3-methylbenzoyl)pyridine (2.10 g, 83%) as a yellow oily material.

REFERENCE EXAMPLE 13

The following compound was obtained in the same manner as described in Reference Example 12.
2-Ethylamino-6-ethyl-3-(3-methylbenzoyl)pyridine

REFERENCE EXAMPLE 14

Diisopropylamine (23 ml, 175 mmol) was added to a tetrahydrofuran (500 ml) solution of 1.6 M hexane solution (100 ml, 160 mmol) of n-butyl lithium at −65° C. or lower, and the mixture was warmed up to −40° C. The reaction solution was mixed with 2-chloropyridine (17 g, 150 mmol) at −70° C. or lower and stirred for 1.5 hours at −70° C. or lower. the reaction solution was mixed with cyclohexanecarbaldehyde (17 g, 151 mmol) at −70° C. or lower and stirred for 2 hours at −70° C. or lower. The reaction solution was mixed with water, warmed to room temperature and then extracted with ethyl acetate. The organic layer was dried over anhydrous magnesium sulfate and concentrated under a reduced pressure. Thereafter, the resulting residue was purified by silica gel column chromatography (chloroform) to give 2-chloro-α-cyclohexyl-3-pyridinemethanol-(17 g, 50%).

REFERENCE EXAMPLE 15

Under an atmosphere of argon, 1.6 M hexane (30 ml) solution of n-butyl lithium was added dropwise to a tetrahydrofuran (200 ml) solution of diisopropylamine (5.52 g, 54.7 mmol) which was cooled at −78° C., and the mixture was stirred for 30 minutes 2-Chloropyridine (5.71 g, 50.3 mmol) was added dropwise to the reaction solution, followed by 90 minutes of stirring. 2-Thiophenecarbaldehyde (6.01 g, 53.7 mmol) was added dropwise to the reaction solution, followed by 30 minutes of stirring. The reaction solution was mixed with brine and extracted with chloroform. The organic layer was washed with brine and dried over anhydrous sodium sulfate. After removing sodium sulfate by filtration, the solvent was evaporated under a reduced pressure, and the resulting residue was purified by silica gel column chromatography (chloroform) to give α-(2-chloropyridin-3-yl)-2-thiophenmethanol (6.66 g, 27.5 mmol, 59%).

The following compounds of Reference Examples 16 to. 20 were obtained in the same manner as described in Reference Example 15.

REFERENCE EXAMPLE 16
α-(2-Chloropyridin-3-yl)-3-thiophenmethanol

REFERENCE EXAMPLE 17
α-(2-Chloropyridin-3-yl-2-thiazolemethanol

REFERENCE EXAMPLE 18
α-(2-Chloropyridin-3-yl)-2-pyridinemethanol

REFERENCE EXAMPLE 19
α-(2-Chloropyridin-3-yl)-3-pyridinemethanol

REFERENCE EXAMPLE 20
α-(2-Chloropyridin-3-yl)-4-pyridinemethanol

REFERENCE EXAMPLE 21

A tetrahydrofuran (30 ml) solution of 2-chloro-6-methylnicotinic acid (3.43 g, 20 mmol) was cooled to −40° C., mixed with ether (30 ml) solution of 2.0 M cyclohexyl magnesium chloride and stirred overnight at room temperature. The reaction solution was poured into saturated ammonium chloride aqueous solution and extracted with ethyl acetate. The organic layer was washed with brine and dried over anhydrous magnesium sulfate. After removing magnesium sulfate by filtration, the filtrate was concentrated under a reduced pressure and the resulting residue was purified by silica gel column chromatography (hexane-ethyl acetate) to give 2-chloro-3-cyclohexylcarbonyl-6-methylpyridine (650 mg, 14%) as a brown oily material.

REFERENCE EXAMPLE 22

Pyridinium chlorochromate (20.0 g, 93 mmol) was added to a dichloromethane (200 ml) solution of 2-chloro-α-cyclohexyl-3-pyridinemethanol (17.0 g, 75 mmol), and the mixture was stirred at room temperature for 4 hours. The reaction solution was mixed with pyridinium chlorochromate (10.0 g, 46 mmol) and stirred for 2 hours at room temperature, and then ether was added to the reaction solution to remove insoluble matter by filtration. The solvent was evaporated under a reduced pressure, and the resulting residue was purified by silica gel column chromatography (hexane-chloroform) to give 2-chloro-3-cyclohexylcarbonylpyridine (14.9 g, 88%) as an oily material.

REFERENCE EXAMPLE 23

To a toluene (100 ml) solution of α-(2-chloropyridin-3-yl)-2-thiophenmethanol (6.14 g, 27.2 mmol) was added 85% manganese dioxide (25 g, 245 mmol), followed by 2 hours of heating under reflux. The reaction solution was passed through celite and the resulting filtrate was concentrated under a reduced pressure. The resulting residue was purified by silica gel column chromatography (hexane-chloroform) to give 2-chloro-3-(2-thiophenecarbonyl)pyridine (5.32 g, 23.8 mmol, 87%).

The following compounds of Reference Examples 24 to 28 were obtained in the same manner as described in Reference Example 23.

REFERENCE EXAMPLE 24
2-Chloro-3-(3-thiophenecarbonyl)pyridine

REFERENCE EXAMPLE 25
2-Chloro-3-(2-thiazolecarbonyl)pyridine

REFERENCE EXAMPLE 26
2-Chloro-3-(2-pyridinecarbonyl)pyridine

REFERENCE EXAMPLE 27
2-Chloro-3-(3-pyridinecarbonyl)pyridine

REFERENCE EXAMPLE 28
2-Chloro-3-(4-pyridinecarbonyl)pyridine

The following compounds of Reference Examples 29 to 36 were obtained in the same manner as described in Reference Example 6.

REFERENCE EXAMPLE 29
3-Cyclohexylcarbonyl-2-ethylamino-6-methylpyridine

REFERENCE EXAMPLE 30
3-Cyclohexylcarbonyl-2-ethylaminopyridine

REFERENCE EXAMPLE 31
2-Ethylamino-3-(2-thiophenecarbonyl)pyridine

REFERENCE EXAMPLE 32
2-Ethylamino-3-(3-thiophenecarbonyl)pyridine

REFERENCE EXAMPLE 33
2-Ethylamino-3-(2-thiazolecarbonyl)pyridine

REFERENCE EXAMPLE 34
2-Ethylamino-3-(2-pyridinecarbonyl)pyridine

REFERENCE EXAMPLE 35
2-Ethylamino-3-(3-pyridinecarbonyl)pyridine

REFERENCE EXAMPLE 36
2-Ethylamino-3-(4-pyridinecarbonyl)pyridine

The following compounds of Reference Examples 37 and 38 were obtained in the same manner as described in Reference Example 15.

REFERENCE EXAMPLE 37
2-Chloro-α-(3-chlorophenyl)-6-trifluoromethyl-3-pyridinemethanol

REFERENCE EXAMPLE 38
α-(3-Bromophenyl)-2-chloro-6-trifluoromethyl-3-pyridinemethanol The following compounds of Reference Examples 39 and 40 were obtained in the same manner as described in Reference Example 23.

REFERENCE EXAMPLE 39
2-Chloro-3-(3-chlorobenzoyl)-6-trifluoromethylpyridine

REFERENCE EXAMPLE 40
3-(3-Bromobenzoyl)-2-chloro-6-trifluoromethylpyridine

The following compounds of Reference Examples 41 and 42 were obtained in the same manner as described in Reference Example 6.

REFERENCE EXAMPLE 41
3-(3-Chlorobenzoyl)-2-ethylamino-6-trifluoromethylpyridine

REFERENCE EXAMPLE 42
3-(3-Bromobenzoyl)-2-ethylamino-6-trifluoromethylpyridine

REFERENCE EXAMPLE 43

2-Amino-3-cyano-6-dimethoxymethylpyridine (39.6 g, 0.2 mol) and 12 ml (0.2 mol) of acetaldehyde were dissolved in 400 ml of acetic acid, and the resulting solution was mixed with 45.5 g (0.2 mol) of sodium triacetoxyborohydride and stirred for 2.5 hours at room temperature. The reaction solution was concentrated under a reduced pressure, diluted with chloroform and then washed with 1 N sodium hydroxide aqueous solution. The organic layer was dried over anhydrous magnesium sulfate, magnesium sulfate was removed by filtration and then the filtrate was concentrated under a reduced pressure. Thereafter, the resulting residue was purified by silica gel column chromatography (hexane-ethyl acetate) to give 33.9 g of 3-cyano-2-ethylamino-6-dimethoxymethylpyridine as an oily material. The yield was 77%.

REFERENCE EXAMPLE 44

Magnesium (18.6 g, 0.76 mol) was added to 500 ml of tetrahydrofuran in which 146.7 g (0.77 mol) of 3-bromochlorobenzene had been dissolved, followed by stirring at room temperature. Since exothermic reaction occurred, the stirring was continued until the exothermicity ceased. The reaction solution was cooled to −20° C., mixed with 33.9 g (0.15 mol) of 3-cyano-2-ethylamino-6-dimethoxymethylpyridine and then heated-overnight under reflux. The reaction solution was mixed with saturated ammonium chloride aqueous solution and extracted with ethyl acetate. The organic layer was washed with water and dried over anhydrous magnesium sulfate. After removing magnesium sulfate by filtration, the solvent was evaporated under a reduced pressure to give crude 3-(3-chlorobenzoyl)-2-ethylamino-6-dimethoxymethylpyridine. The crude 3-(3-chlorobenzoyl)-2-ethylamino-6-dimethoxymethylpyridine was diluted with 500 ml of tetrahydrofuran, mixed with 6 N hydrochloric acid and then stirred at room temperature for 6 hours. The reaction mixture was adjusted to pH 10 with sodium hydroxide aqueous solution and extracted with ethyl acetate. The organic layer was dried over anhydrous magnesium sulfate, magnesium sulfate was removed by filtration and then the resulting filtrate was concentrated under a reduced pressure. Thereafter, the resulting residue was purified by silica gel column chromatography (hexane-ethyl acetate) to give 3-(3-chlorobenzoyl)-2-ethylaminopyridine-6-carbaldehyde. Reference Exampel 45

α-(3-Chlorobenzoyl)acetamide (19.76 g, 0.1 mol) was dissolved in 250 ml of ethanol, and the solution was mixed with 19.15 g (0.11 mol) of 1,1-diethoxy-3-pentanone and heated under reflux for 40 hours. After cooling to room temperature, the reaction solution was poured into ice water and extracted with chloroform. The organic layer was washed with 1 N hydrochloric acid, brine and dried over anhydrous magnesium sulfate, magnesium sulfate was removed by filtration and then the resulting filtrate was concentrated under a reduced pressure. Thereafter, the resulting residue was mixed with diethyl ether and the thus formed crystals were collected by filtration and washed with diethyl ether to give 18.50 g of 3-(3-chlorobenzoyl)-6-ethyl-2-pyridone in the form of crystals. The yield was 71%.

The following compounds of Reference Examples 46 and 47 were obtained in the same manner as described in Reference Example 45.

REFERENCE EXAMPLE 46
3-(3-Chlorobenzoyl)-6-phenyl-2-pyridone

REFERENCE EXAMPLE 47
3-(3-Chlorobenzoyl)-6-cyclopropyl-2-pyridone

REFERENCE EXAMPLE 48
3-(3-Chlorobenzoyl)-6-ethyl-2-pyridone (95.8 g, 366 mmol) was dissolved in 1,000 ml of dichloroethane, 56.4 ml (403 mmol) of triethylamine, 4.52 g (366 mmol) of 4-dimethylaminopyridine and 76.7 g (403 mmol) of p-toluenesulfonyl chloride were added thereto, followed by stirring at room temperature for 1 hour. The reaction solution was washed with water, 1 N hydrochloric acid-brine and dried over anhydrous magnesium sulfate. Magnesium sulfate was removed by filtration and then the resulting filtrate was concentrated under a reduced pressure. Thereafter, the resulting residue was recrystallized from ethyl acetate-hexane to give 139.90 g of 3-(3-chlorobenzoyl)-6-ethyl-2-pyridyl p-toluenesulfonate in the form of crystals. The yield was 91.9%.

The following compounds of Reference Examples 49 and 50 were obtained in the same manner as described in Reference Example 48.

REFERENCE EXAMPLE 49
3-(3-Chlorobenzoyl)-6-phenyl-2-pyridyl p-toluenesulfonate

REFERENCE EXAMPLE 50
3-(3-Chlorobenzoyl)-6-cyclopropyl-2-pyridyl p-toluenesulfonate

REFERENCE EXAMPLE 51
3-(3-Chlorobenzoyl)-6-ethyl-2-pyridyl p-toluenesulfonate (26.20 g, 63 mmol) was dissolved in 400 ml of toluene, and the solution was mixed with 50 ml of 70% ethylamine aqueous solution and heated under reflux for 4 hours. After cooling to room temperature, the reaction solution was concentrated under a reduced pressure, diluted with diethyl ether and then washed with water and saturated sodium bicarbonate aqueous solution. The organic layer was dried over anhydrous magnesium sulfate, magnesium sulfate was removed by filtration and then the solvent was evaporated under a reduced pressure to give 19.50 g of 3-(3-chlorobenzoyl)- 6-ethyl-2-ethylaminopyridine as an oily material. The yield was 100%.

The following compounds of Reference Examples 52 and 53 were obtained in the same manner as described in Reference Example 51.

REFERENCE EXAMPLE 52
3-(3-Chlorobenzoyl)-2-ethylamino-6-phenylpyridine

REFERENCE EXAMPLE 53
3-(3-Chlorobenzoyl)-6-cyclopropyl-2-ethylaminopyridine

The following compounds of Reference Examples 54 and 55 were obtained in the same manner as described in Reference Example 45.

REFERENCE EXAMPLE 54
6-Ethyl-3-[(3-methylcyclohexyl)carbonyl]-2-pyridone

REFERENCE EXAMPLE 55
6-Methyl-3-[(3-methylcyclohexyl)carbonyl]-2-pyridone

REFERENCE EXAMPLE 56
6-Ethyl-3-[(3-methylcyclohexyl)carbonyl]-2-pyridone (4.16 g, 17.9 mmol) was dissolved in 100 ml of 1,2-dichloroethane, and the solution was mixed with 6.0 ml (43 mmol) of triethylamine, 600 mg (492 mmol) of 4-dimethylaminopyridine and 6.00 q (31.6 mmol) of p-toluenesulfonyl chloride and stirred for 2 hours at an oil temperature of 70° C. After cooling to room temperature, this was mixed with water and extracted with chloroform. The organic layer was washed with 1 N hydrochloric acid, saturated sodium bicarbonate aqueous solution and brine in that order, dried over anhydrous magnesium sulfate and, after removing magnesium sulfate by filtration, concentrated under a reduced pressure to give 7.80 g of partially purified 6-ethyl-3-[(3-methylcyclohexyl)carbonyl]-2-pyridyl p-toluenesulfonate. The thus partially purified product was dissolved in 100 ml of toluene, and the solution was mixed with 20 ml of 70% ethylamine aqueous solution and heated under reflux for 8 hours. Then, 20 ml of 70% ethylamine aqueous solution was added, followed by overnight heating under reflux. After cooling to room temperature, this was adjusted to pH 1 by adding 1 N hydrochloric acid and stirred for 15 minutes. This was neutralized with 1 N sodium hydroxide aqueous solution and then extracted with chloroform. The organic layer was washed with brine, dried over anhydrous sodium sulfate and then, after removing sodium sulfate by filtration, concentrated under a reduced pressure. Thereafter, the resulting residue was purified by silica gel column chromatography (ethyl acetate-hexane) to give 2.60 g of 6-ethyl-2-ethylamino-3-[(3-methylcyclohexyl)carbonyl]pyridine. The yield was 56%.

REFERENCE EXAMPLE 57

The following compound was obtained in the same manner as described in Reference Example 56.
6-Methyl-2-ethylamino-3-[(3-methylcyclohexyl)carbonyl]pyridine The following compounds of Reference Examples 58 and 59 were obtained in the same manner as described in Reference Example 4.

REFERENCE EXAMPLE 58
2-Chloro-3-(3-chlorobenzoyl)-6-methylpyridine

REFERENCE EXAMPLE 59
2-Chloro-6-methyl-3-(3-methylbenzoyl)pyridine

The following compounds of Reference Examples 60 to 63 were obtained in the same manner as described in Reference Example 6.

REFERENCE EXAMPLE 60
3-(3-Chlorobenzoyl)-6-methyl-2-(propylamino)pyridine

REFERENCE EXAMPLE 61
3-(3-Chlorobenzoyl)-2-(cyclopropylmethylamino)-6-methylpyridine

REFERENCE EXAMPLE 62
6-Methyl-2-(propylamino)-3-(3-methylbenzoyl)pyridine

REFERENCE EXAMPLE 63
2-(Cyclopropylmethylamino)-6-methyl-3-(3-methylbenzoyl)pyridine

REFERENCE EXAMPLE 64

The following compound was obtained in the same manner as described in Reference Example 4.
3-Benzoyl-2-chloro-6-methylpyridine

REFERENCE EXAMPLE 65

3-Benzoyl-2-chloro-6-methylpyridine (3.00 g, 12.9 mmol) dissolved in 40 ml of concentrated sulfuric acid was cooled to 5° C. or lower, 1.0 ml of fuming nitric acid was slowly added dropwise thereto, followed by stirring for 30 minutes. The reaction solution was poured into ice water, neutralized with sodium hydroxide aqueous solution and then extracted with ethyl acetate. The organic layer was washed with brine and dried over anhydrous magnesium sulfate. After removing magnesium sulfate by filtration, the solvent was evaporated under a reduced pressure and the resulting residue was recrystallized from ethyl aretate-diisopropyl ether to give 1.81 g (51%) of 2-chloro-6-methyl-3-(3-nitrobenzoyl)pyridine.

REFERENCE EXAMPLE 66

The following compound was obtained in the same manner as described in Reference Example 6.
2-Ethylamino-6-methyl-3-(3-nitrobenzoyl)pyridine

REFERENCE EXAMPLE 67

The following compound was obtained in the same manner as described in Reference Example 45.
6-Methyl-3-(1-naphthylcarbonyl)-2-pyridone

REFERENCE EXAMPLE 68

The following compound was obtained in the same manner as described in Reference Example 48.
6-Methyl-3-(1-naphthylcarbonyl)-2-pyridyl p-toluenesulfonate

REFERENCE EXAMPLE 69

The following compound was obtained in the same manner as described in Reference Example 51.
2-Ethylamino-6-methyl-3-(1-naphthylcarbonyl)pyridine
Example 1

Chlorosulfonyl isocyanate (0.8 ml, 9 mmol) was added to a tetrahydrofuran (50 ml) solution of 3-(3-chlorobenzoyl)-6-ethyl-2-ethylaminopyridine (2.6 g, 9 mmol) under ice-cooling, followed by stirring for 1 hour under ice-cooling. To the reaction solution were added water and saturated sodium bicarbonate aqueous solution in that order, followed by 30 minutes of stirring at room temperature. This was adjusted to pH 10 with 1 N sodium hydroxide aqueous solution and extracted with chloroform. After drying the organic layer over anhydrous magnesium sulfate, magnesium sulfate was removed by filtration and the resulting filtrate was concentrated under a reduced pressure. Thereafter, the resulting residue was purified by silica gel column chromatography (hexane-ethyl acetate) to give 4-(3-chlorophenyl)-1,7-diethylpyrido[2,3-d]pyrimidin-2(1H)-one (1.7 g, 60%) in the form of crystals.

The following compounds of Examples 2 to 8 were obtained in the same manner as described in Example 1.

EXAMPLE 2
4-(3-Bromophenyl)-1,7-diethylpyrido[2,3-d]pyrimidin-2(1H)-one

EXAMPLE 3
4-(3-Chlorophenyl)-1-ethyl-7-methylpyrido[2,3-d]pyrimidin-2(1H)-one

EXAMPLE 4
4-(3-Bromophenyl)-1-ethyl-7-methylpyrido[2,3-d]pyrimidin-2(1H)-one

EXAMPLE 5
1-Ethyl-7-methyl-4-(3-methylphenyl)-pyrido[2,3-d]pyrimidin-(1H)-one

EXAMPLE 6
1,7-Diethyl-4-(3-methylphenyl)pyrido[2,3-d]pyrimidin-2(1H)-one

EXAMPLE 7
4-Cyclohexyl-1-ethyl-7-methylpyrido[2,3-d]pyrimidin-2(1H)-one

EXAMPLE 8
4-Cyclohexyl-1-ethylpyrido[2,3-d]pyrimidin-2(1H)-one

EXAMPLE 9

Chlorosulfonyl isocyanate (0.5 ml, 5.6 mmol) was added to a solution of 2-ethylamino-3-(2-thiophenecarbonyl)

pyridine (1.01 g, 4.35 mmol) in tetrahydrofuran (50 ml) under ice-cooling, followed by stirring for 30 minutes. The reaction solution was mixed with water and extracted with chloroform. The organic layer was washed with brine and dried over anhydrous sodium sulfate. After removing sodium sulfate by filtration, the resulting filtrate was concentrated under a reduced pressure and the resulting residue was purified by silica gel column chromatography (chloroform-ethyl acetate) and recrystallized from ethyl acetate to give 1-ethyl-4-(2-thienyl)pyrido[2,3-d]pyrimidin-2(1H)-one (613 mg, 2.38 mmol, 55%).

The following compounds of Examples 10 to 16 were obtained in the same manner as described in Example 9.

EXAMPLE 10
1-Ethyl-4-(3-thienyl)pyrido[2,3-d]pyrimidin-2(1H)-one

EXAMPLE 11
1-Ethyl-4-(2-thiazolyl)pyrido[2,3-d]pyrimidin-2(1H)-one

EXAMPLE 12
1-Ethyl-4-(2-pyridyl)pyrido[2,3-d]pyrimidin-2(1H)-one

EXAMPLE 13
1-Ethyl-4-(3-pyridyl)pyrido[2,3-d]pyrimidin-2(1H)-one

EXAMPLE 14
1-Ethyl-4-(4-pyridyl)pyrido[2,3-d]pyrimidin-2(1H)-one

EXAMPLE 15
4-(3-Chlorophenyl)-1-ethyl-7-trifluoromethylpyrido[2,3-d]pyrimidin-2(1H)-one

EXAMPLE 16
4-(3-Bromophenyl)-1-ethyl-7-trifluoromethylpyrido[2,3-d]pyrimidin-2(1H)-one

EXAMPLE 17

The following compound was obtained in the same manner as described in Example 1.
4-(3-Chlorophenyl)-1-ethyl-2-oxo-1,2-dihydropyrido[2,3-d]pyrimidin-7-carbaldehyde

EXAMPLE 18

Sodium borohydride (35 mg, 0.9 mmol) was added to a mixture of 1.16 g (3.7 mmol) of 4-(3-chlorophenyl)-1-ethylpyrido[2,3-d]pyrimidin-2(1H)-one-7-carbaldehyde and 20 ml of ethanol under ice-cooling, followed by stirring for 30 minutes under ice-cooling. The reaction solution was mixed with acetone and concentrated under a reduced pressure, and the resulting residue was mixed with water and extracted with chloroform. The chloroform layer was dried over anhydrous magnesium sulfate, magnesium sulfate was removed by filtration and the resulting filtrate was concentrated under a reduced pressure. Thereafter, the resulting residue was purified by silica gel column chromatography (hexane-ethyl acetate-chloroform) and further recrystallized from acetonitrile-ethanol to give 271 mg of 4-(3-chlorophenyl)-1-ethyl-7-hydroxymethylpyrido[2,3-d]pyrimidin-2(1H)-one. The yield was 23%.

EXAMPLE 19

1 M Methylmagnesium bromide (14 ml, 14 mmol) was added to a solution of 4.4 g (14 mmol) of 4-(3-chlorophenyl)-1-ethylpyrido[2,3-d]pyrimidin-2(1H)-one-7-carbaldehyde in 50 ml of tetrahydrofuran under ice-cooling, followed by stirring for 30 minutes under ice-cooling. Then, 7 ml (7 mmol) of 1 M methylmagnesium bromide was added and the mixture was stirred for 30 minutes under ice-cooling. Then, saturated ammonium chloride aqueous solution was added, followed by extraction with chloroform. The organic layer was dried over anhydrous magnesium sulfate, magnesium sulfate was removed by filtration and the resulting filtrate was concentrated under a reduced pressure. Thereafter, the resulting residue was purified by silica gel column chromatography (hexane-ethyl acetate-chloroform) to give 1.4 g of 4-(3-chlorophenyl)-1-ethyl-7-(1-hydroxyethyl)pyrido[2,3-d]pyrimidin-2(1H)-one. The yield was 30%.

EXAMPLE 20

Manganese dioxide (1.00 g) was added to a solution of 366 mg (1.1 mmol) of 4-(3-chlorophenyl)-1-ethyl-7-(1-hydroxyethyl)pyrido[2,3-d]pyrimidin-2(1H)-one dissolved in 20 ml of chloroform, and the mixture was heated under reflux for 1 hour. The reaction solution was mixed with 1.00 g of manganese dioxide and heated under reflux for 1 hour and then again mixed with 500 mg of manganese dioxide and heated under reflux for 1 hour. After removing insoluble matter by filtration, the filtrate was concentrated under a reduced pressure and the resulting residue was purified by silica gel column chromatography (hexane-ethyl acetate-chloroform) to give 303 mg of 7-acetyl-4-(3-chlorophenyl)-1-ethylpyrido[2,3-d]pyrimidin-2(1H)-one. The yield was 84%.

The following compounds of Examples 21 and 22 were obtained in the same manner as described in Example 1.

EXAMPLE 21
4-(3-Chlorophenyl)-1-ethyl-7-phenylpyrido[2,3-d]pyrimidin-2(1H)-one

EXAMPLE 22
4-(3-Chlorophenyl)-7-cyclopropyl-1-ethylpyrido[2,3-d]pyrimidin-2(1H)-one

EXAMPLE 23

N-Bromosuccinimide (8.94 g, 50.2 mmol) and 200 mg of 2,2'-azobis(isobutyronitrile) were added to a solution of 15.0 g (47.8 mmol) of 4-(3-chlorophenyl)-1,7-diethylpyrido[2,3-d]pyrimidin-2(1H)-one in 150 ml of carbon tetrachloride, followed by heating under reflux for 3 hours. The reaction solution was again mixed with 1.28 g (7.17 mmol) of N-bromosuccinimide and 100 mg of 2,2'-azobis (isobutyronitrile), followed by heating under reflux for 1 hour. After cooling to room temperature, insoluble matter was removed by filtration, and the resulting filtrate was mixed with water and extracted with carbon tetrachloride. The organic layer was washed with brine and dried over anhydrous magnesium sulfate. After removing magnesium sulfate by filtration, the filtrate was concentrated under a reduced pressure and the resulting residue was purified by silica gel column chromatography (hexane-ethyl acetate) to give 11.5 g of 7-(1-bromoethyl)-4-(3-chlorophenyl)-1-ethylpyrido[2,3-d]pyrimidin-2(1H)-one in the form of crystals. The yield was 61%.

EXAMPLE 24

N-Bromosuccinimide (590 mg, 3.3 mmol) and 10 mg of 2,2'-azobis(isobutyronitrile) were added to a solution of 940 mg (3 mmol) of 4-(3-chlorophenyl)-1,7-diethylpyrido[2,3-d]pyrimidin-2(1H)-one in 20 ml of carbon tetrachloride, followed by heating under reflux for 5 hours. The reaction solution was again mixed with 210 mg (1.2 mmol) of N-bromosuccinimide and heated overnight under reflux. Insoluble matter was removed by filtration, and the resulting filtrate was mixed with water and extracted with carbon tetrachloride. The organic layer was washed with brine and dried over anhydrous magnesium sulfate, magnesium sulfate was removed by filtration, and the resulting filtrate was concentrated under a reduced pressure. The thus obtained residue was mixed with 10 ml of methanol and 300 mg of sodium acetate and heated overnight under reflux. The reaction solution was diluted with chloroform and washed with water and brine. The organic layer was dried over anhydrous magnesium sulfate, magnesium sulfate was removed by filtration, and then the resulting filtrate was concentrated under a reduced. pressure. Thereafter, the resulting residue was purified by silica gel column chromatography (hexane-ethyl acetate) to give 520 mg of 7-(1-acetoxyethyl)-4-(3-chlorophenyl)-1-ethylpyrido[2,3-d] pyrimidin-2(1H)-one in the form of crystals. The yield was 47%.

EXAMPLE 25

Methanol (30 ml) and 30 ml of 1 N sodium hydroxide aqueous solution were added to 6.78 g (18.2 mmol) of 7-(1-acetoxyethyl)-4-(3-chlorophenyl)-1-ethylpyrido[2,3-d] pyrimidin-2(1H)-one, followed by stirring for 20 minutes at room temperature. The reaction solution was neutralized by adding 1 N hydrochloric acid and extracted with chloroform. The organic layer was washed with brine and dried over anhydrous magnesium sulfate, magnesium sulfate was removed by filtration and the resulting filtrate was concentrated under a reduced pressure. Thereafter, the resulting residue was purified by silica gel column chromatography (chloroform) to give 4.50 g of 4-(3-chlorophenyl)-1-ethyl-7-(1-hydroxyethyl)pyrido[2,3-d]pyrimidin-2(1H)-one in the form of crystals. The yield was 75%.

The following compounds of Examples 26 and 27 were obtained in the same manner as described in Example 1.

EXAMPLE 26

1-Ethyl-7-methyl-4-(3-methylcyclohexyl)-pyrido[2,3-d] pyrimidin-2(1H)-one

EXAMPLE 27

1,7-Diethyl-4-(3-methylcyclohexyl)-pyrido[2,3-d] pyrimidin-2(1H)-one

EXAMPLE 28

Diphosphorus pentasulfide (3.00 g, 13.5 mmol) was added to a solution of 2.00 g (6.69 mmol) of 4-(3-chlorophenyl)-1-ethyl-7-methylpyrido[2,3-d]pyrimidine in 100 ml of 1,2-dichloroethane, followed by heating under reflux for 6 hours. The reaction solution was cooled to room temperature, mixed with saturated sodium bicarbonate and extracted with chloroform. The organic layer was washed with brine and dried over anhydrous magnesium sulfate, magnesium sulfate was removed by filtration and the resulting filtrate was concentrated under a reduced pressure. Thereafter, the resulting residue was purified by silica gel column chromatography (hexane-chloroform) and further recrystallized from ethyl acetate-diisopropyl ether to give 1.14 g of 4-(3-chlorophenyl)-1-ethyl-7-methylpyrido[2,3-d] pyrimidin-2(1H)-thione. The yield was 54%.

The following compounds of Examples 29 to 34 were obtained in the same manner as described in Example 1.

EXAMPLE 29

4-(3-Bromophenyl)-6,7-dimethyl-1-ethylpyrido[2,3-d] pyrimidin-2(1H)-one

EXAMPLE 30

4-(3-Chlorophenyl)-7-methyl-1-propylpyrido[2,3-d] pyrimidin-2(1H)-one

EXAMPLE 31

4-(3-Chlorophenyl)-1-cyclopropylmethyl-7-methylpyrido [2,3-d]pyrimidin-2(1H)-one

EXAMPLE 32

7-Methyl-4-(3-methylphenyl)-1-propylpyrido[2,3-d] pyrimidin-2(1H)-one

EXAMPLE 33

1-Cyclopropylmethyl-7-methyl-4-(3-methylphenyl)pyrido [2,3-d]pyrimidin-2(1H)-one

EXAMPLE 34

4-Cyclohexyl-1,7-diethylpyrido[2,3-d]pyrimidin-2(1H)-one

EXAMPLE 35

The following compound was obtained as a by-product of Example 5.
6-Chloro-1-ethyl-7-methyl-4-(3-methylphenyl)pyrido[2,3-d]pyrimidin-2(1H)-one

EXAMPLE 36

4-(3-Chlorophenyl)-1-ethyl-2-oxo-1,2-dihydropyrido[2,3-d]pyrimidine-7-carbaldehyde (900 mg, 2.9 mmol) was dissolved in 10 ml of methanol, 420 mg (6.0 mmol) of hydroxylamine hydrochloride and 550 mg (6.7 mmol) of sodium acetate were added thereto, followed by stirring overnight at room temperature. The insoluble matter was washed with water and chloroform and recrystallized from dimethylformamide-acetonitrile to give 171 mg (18%) of 4-(3-chlorophenyl)-1-ethyl-7-hydroxyiminomethylpyrido [2,3-d]pyrimidin-2(1H)-one.

EXAMPLE 37

The following compound was obtained in the same manner as described in Example 1.
1-Ethyl-7-methyl-4-(3-nitrophenyl)-pyrido[2;3-d] pyrimidin-2(1H)-one

EXAMPLE 38

The following compound was obtained in the same manner as described in Example 23.
7-Bromomethyl-4-(3-chlorophenyl)-1-ethylpyrido[2,3-d] pyrimidin-2(1H)-one

EXAMPLE 39

The following compound was obtained as a by-product of Example 1.
6-Chloro-4-(3-chlorophenyl)-1,7-diethylpyrido[2,3-d] pyrimidin-2(1H)-one

EXAMPLE 40

Potassium thioacetate (0.54 g, 48 mmol) was added to 7-(1-bromoethyl)-4-(3-chlorophenyl)-1-ethylpyrido[2,3-d] pyrimidin-2(1H)-one (1.57 g, 40 mmol) dissolved in dimethylformamide (16 ml), followed by stirring at room temperature for 2 hours. The reaction solution was mixed with ethyl acetate, washed with water and with brine, and dried over anhydrous magnesium sulfate. The magnesium sulfate was removed by filtration and the filtrate was concentrated under reduced pressure. The residue was purified by silica gel column chromatography (hexane-ethyl acetate) to give 7-(1-acetylthioethyl)-4-(3-chlorophenyl)-1-ethylpyrido[2,3-d]pyrimidin-2(1H)-one (1.13 g, 73%).

EXAMPLE 41

The following compound was obtained in the same manner as described in Example 28.
4-(3-Chlorophenyl)-1,7-diethylpyrido[2,3-d]pyrimidin-2(1H)-thione

EXAMPLE 42

The following compound was obtained in the same manner as described in Example 1.
1-Ethyl-7-methyl-4-(1-naphthyl)pyrido[2,3-d]pyrimidin-2(1H)-one

EXAMPLE 43

7-Acetyl-4-(3-chlorophenyl)-1-ethylpyrido[2,3-d]pyrimidin-2(1H)-one (1.62 g, 495 mmol) and 30 ml of methyl orthoformate were dissolved in 30 ml of methanol, a catalytically effective amount of Dowex-50W-X4 was added thereto, followed by heating overnight under reflux. After cooling to room temperature, insoluble matter was removed by filtration and the solvent was evaporated under a reduced pressure. The resulting residue was purified by silica gel column chromatography (toluene-ethyl acetate) and recrystallized from diisopropyl ether to give 1.27 g (69%) of 4-(3-chlorophenyl)-1-ethyl-7-(1,1-dimethoxyethyl)pyrido[2,3-d]pyrimidin-2(1H)-one.

Physical properties of the compounds obtained in Reference Examples and Examples are shown in Tables 3 and 4.

In the Tables, Rex. No. means Reference Number; Ex. No. means Example Number; NMR means nuclear magnetic resonance spectrum measured at 400 MHz and at room temperature using TMS as the internal standard and using DMSO-$d_6$ (Reference Examples 45 to 47) or CDCl$_3$ (all Examples and Reference Examples other than Reference Examples 45 to 47) as a solvent for NMR; mp. means melting point; and Anal. means elemental analysis data; calcd. means the calculated value, found means the experimentally found value; Et means an ethyl group; Ac means an acetyl group; iPr means an isopropyl group; and dec. means decomposition.

TABLE 3

| Rex. No. | NMR |
|---|---|
| 1 | δ: 1.33(3H, t, J=7.3Hz), 2.88(2H, q, J=7.3Hz), 7.23(1H, d, J=7.9Hz), 7.89(1H, d, J=7.9Hz) |
| 2 | δ: 1.36(3H, t, J=7.3Hz), 2.90(2H, q, J=7.3Hz), 7.26(1H, m), 7.43(1H, t, J=7.9Hz), 7.59(1H, m), 7.65–7.70(2H, m), 7.79 (1H, t, J=1.8Hz) |
| 3 | δ: 1.37(3H, t, J=7.9Hz), 2.91(2H, q, J=7.9Hz), 7.25(1H, d, J=7.9Hz), 7.37(1H, t, J=7.9Hz), 7.68(1H, d, J=7.9Hz), 7.70 (1H, d, J=7.9Hz), 7.73–7.76(1H, m), 7.95(1H, s) |
| 4 | δ: 2.64(3H, s), 7.24(1H, d, J=7.3Hz), 7.43(1H, t, J=7.9Hz), 7.60(1H, m), 7.65(2H, m), 7.78(1H, s) |
| 5 | δ: 2.64(3H, s), 7.24(1H, d, J=7.9Hz), 7.36(1H, t, J=7.9Hz), 7.65(1H, d, J=7.9Hz), 7.69(1H, d, J=7.9Hz), 7.74(1H, d, J=7.9Hz), 7.94(1H, s) |
| 6 | δ: 1.29(3H, t, J=7.9Hz), 1.31(3H, t, J=7.5Hz), 2.70(2H, q, J=7.5Hz), 3.66(2H, m), 6.34(1H, d, J=8.0Hz), 7.35–7.60(5H, m), 8.83(1H, brs) |
| 7 | δ: 1.27–1.33(6H, m), 2.70(2H, q, J=7.9Hz), 3.62–3.68(2H, m), 6.34(1H, d, J=7.9Hz), 7.32(1H, t, J=7.9Hz), 7.45(1H, d, J=7.3Hz), 7.57(1H, d, J=7.9Hz), 7.62(1H, dd, J=7.9, 1.8Hz), 7.68(1H, d, J=1.8Hz), 8.83(1H, brs) |
| 8 | δ: 1.31(3H, t, J=7.0Hz), 2.44(3H, s), 3.64(2H, m), 6.33(1H, d, J=7.9Hz), 7.35–7.60(5H, m), 8.84(1H, brs) |
| 9 | δ: 1.31(3H, t, J=7.3Hz), 2.44(3H, s), 3.64(2H, m), 6.33(1H, d, J=7.9Hz), 7.32(1H, t, J=7.9Hz), 7.45(1H, d, J=7.3Hz), 7.55 (1H, d, J=7.9Hz), 7.63(1H, dd, J=7.9, 1.2Hz), 7.68(1H, s), 8.83(1H, brs) |
| 10 | δ: 2.40(3H, s), 2.63(3H, s), 7.22(1H, d, J=7.3Hz), 7.36(1H, t, J=7.3Hz), 7.43(1H, d, J=7.3Hz), 7.57(1H, d, J=7.3Hz), 7.60–7.65(2H, m) |
| 11 | δ: 1.36(3H, t, J=7.9Hz), 2.41(3H, s), 2.90(2H, q, J=7.9Hz), 7.22(1H, d, J=7.9Hz), 7.34–7.44(2H, m), 7.57(1H, d, J=7.9Hz), 7.64–7.65(2H, m) |
| 12 | δ: 1.31(3H, t, J=7.3Hz), 2.40(3H, s), 2.43(3H, s), 3.63(2H, m), 6.31(1H, d, J=7.9Hz), 7.32(3H, s), 7.36(1H, s), 7.61(1H, d, J=7.9Hz), 8.85(1H, brs) |
| 13 | δ: 1.28–1.32(6H, m), 2.40(3H, s), 2.69(2H, q, J=7.3Hz), 3.62–3.68(2H, m), 6.32(1H, d, J=7.9Hz), 7.30–7.36(4H, m), 7.63(1H, d, J=7.9Hz), 8.84(1H, brs) |
| 14 | δ: 1.10–1.30(5H, m), 1.60–1.80(6H, m), 2.27(1H, d, J=4.3Hz), 4.88(1H, t, J=4.9Hz), 7.26(1H, dd, J=7.3, 4.9Hz), 7.86(1H, dd, J=7.3, 1.8Hz), 8.27(1H, dd, J=4.9, 1.8Hz) |
| 15 | δ: 3.05(1H, d, J=3.3Hz), 6.38(1H, d, J=3.3Hz), 6.93–6.98(2H, m), 7.26–7.32(2H, m), 8.09(1H, dd, J=7.9, 1.8Hz), 8.29(1H, dd, J=4.9, 1.8Hz) |
| 16 | δ: 3.07(1H, d, J=3.7Hz), 6.21(1H, d, J=3.7Hz), 7.02(1H, dd, J=4.9, 1.2Hz), 7.20(1H, d, J=3.0Hz), 7.24–7.28(2H, m), 7.99 (1H, dd, J=7.9, 1.8Hz), 8.25(1H, dd, J=4.9, 1.8Hz) |
| 17 | δ: 4.99(1H, brs), 6.43(1H, s), 7.30–7.34(2H, m), 7.74(1H, d, J=3.1Hz), 8.01(1H, dd, J=7.9, 1.8Hz), 8.36(1H, dd, J=4.9, 1.8Hz) |
| 18 | δ: 5.56(1H, brs), 6.22(1H, s), 7.15–7.26(2H, m), 7.34(1H, J=7.9Hz), 7.63–7.74(1H, m), 7.81(1H, dd, J=7.9, 1.8Hz), 8.31(1H, dd, J=4.9, 1.8Hz), 8.58(1H, d, J=4.3Hz) |
| 19 | δ: 5.04(1H, brs), 6.14(1H, s), 7.25(1H, dd, J=7.9, 4.9Hz), 7.32 (1H, dd, J=7.9, 4.9Hz), 7.67(1H, d, J=7.9Hz), 8.08(1H, dd, J=7.9, 1.8Hz), 8.30(1H, dd, J=4.9, 1.8Hz), 8.39(1H, d, J=4.9Hz), 8.69(1H, s) |
| 20 | δ: 4.66(1H, brs), 6.18(1H, s), 7.29(1H, dd, J=7.9, 4.9Hz), 7.34 (2H, d, J=7.2Hz), 7.92(1H, dd, J=7.9, 1.8Hz), 8.31(1H, dd, J=4.9, 1.8Hz), 8.46(2H, m) |
| 21 | δ: 1.00–2.10(10H, m), 2.57(3H, s), 3.10(1H, m), 7.22(1H, d, J=7.7Hz), 7.60(1H, d, J=7.7Hz) |
| 22 | δ: 1.20–1.50(5H, m), 1.60–2.00(5H, m), 3.11(1H, m), 7.31(1H, dd, J=7.3, 4.9Hz), 7.67(1H, dd, J=7.3, 1.8Hz), 8.46(1H, dd, J=4.9, 1.8Hz) |
| 23 | δ: 7.16(1H, dd, J=4.9, 2.7Hz), 7.37–7.44(2H, m), 7.78–7.82 (2H, m), 8.55(1H, dd, J=4.9, 1.8Hz) |
| 24 | δ: 7.21–7.43(2H, m), 7.55–7.57(1H, m), 7.76(1H, dd, J=7.3, 1.8Hz), 7.84–7.85(1H, m), 8.55(1H, dd, J=4.9, 1.8Hz) |
| 25 | δ: 7.39(1H, dd, J=7.9, 4.9Hz), 7.81(1H, d, J=3.1Hz), 8.03(1H, dd, J=7.9, 1.8Hz), 8.07(1H, d, J=3.1Hz), 8.57(1H, dd, J=4.9, 1.8Hz) |
| 26 | δ: 7.38(1H, dd, J=7.9, 4.9Hz), 7.50–7.53(1H, m), 7.86(1H, dd, J=7.9, 1.8Hz), 7.94(1H, m), 8.18(1H, d, J=7.9Hz), 8.52(1H, dd, J=4.9, 1.8Hz), 8.65(1H, d, J=1.8Hz) |
| 27 | δ: 7.44(1H, dd, J=7.3, 4.9Hz), 7.48(1H, dd, J=7.3, 4.9Hz), 7.80 (1H, dd, J=7.3, 1.8Hz), 8.14–8.16(1H, m), 8.60(1H, dd, J=4.9, 1.8Hz), 8.85(1H, dd, J=4.9, 1.8Hz), 8.94(1H, d, J=1.8Hz) |
| 28 | δ: 7.37(1H, dd, J=7.9, 4.9Hz), 7.51–7.52(2H, m), 7.73(1H, dd, J=7.9, 1.8Hz), 8.53(1H, dd, J=4.9, 1.8Hz), 8.74–8.78(2H, m) |
| 29 | δ: 1.26(3H, t, J=7.5Hz), 1.30–1.90(10H, m), 2.41(3H, s), 3.20 (1H, m), 3.50–3.60(2H, m), 6.35(1H, d, J=8.5Hz), 7.88(1H, d, J=8.5Hz), 9.09(1H, brs) |
| 30 | δ: 1.20–1.60(8H, m), 1.70–1.90(5H, m), 3.24(1H, m), 3.54(2H, m), 6.51(1H, dd, J=7.9, 4.9Hz), 8.01(1H, dd, J=7.9, 1.8Hz), 8.29(1H, dd, J=4.9, 1.8Hz), 9.07(1H, brs) |
| 31 | δ: 1.29(3H, t, J=7.3Hz), 3.55–3.59(2H, m), 6.55(1H, dd, J=7.9, 4.9Hz), 7.14(1H, dd, J=4.9, 3.7Hz), 7.51(1H, dd, J=3.7, 1.2Hz), 7.67(1H, d, J=4.3Hz), 8.08(1H, dd, J=7.9, 1.8Hz), 8.29(1H, brs), 8.33(1H, dd, J=4.9, 1.8Hz) |
| 32 | δ: 1.31(3H, t, J=7.3Hz), 3.56–3.61(2H, m), 6.51(1H, dd, J=7.9, 4.9Hz), 7.37–7.39(1H, m), 7.40–7.43(1H, m), 7.73–7.74(1H, m), 7.94(1H, dd, J=7.9, 1.8Hz), 8.32(1H, dd, J=4.9, 1.8Hz), |

TABLE 3-continued

| Rex. No. | NMR |
|---|---|
| | 8.58(1H, brs) |
| 33 | δ: 1.32(3H, t, J=7.3Hz), 3.61–3.67(2H, m), 6.62(1H, dd, J=7.9, 4.9Hz), 7.66(1H, d, J=3.1Hz), 8.03(1H, d, J=3.1Hz), 8.37(1H, dd, J=4.9, 1.8Hz), 9.02(1H, brs), 9.43(1H, dd, J=4.9, 1.8Hz) |
| 34 | δ: 1.33(3H, t, J=7.3Hz), 3.61–3.67(2H, m), 6.50(1H, dd, J=7.9, 4.9Hz), 7.43(1H, dd, J=7.9, 4.9Hz), 7.78(1H, d, J=7.9Hz), 7.86–7.89(1H, m), 8.13(1H, dd, J=7.9, 1.8Hz), 8.33(1H, dd, J=4.9, 1.8Hz), 8.67(1H, d, J=4.9Hz), 8.94(1H, brs) |
| 35 | δ: 1.33(3H, t, J=7.3Hz), 3.62–3.67(2H, m), 6.50(1H, dd, J=7.9, 4.9Hz), 7.42(1H, dd, J=7.3, 4.9Hz), 7.68(1H, dd, J=7.9, 1.8Hz), 7.90(1H, d, J=7.3Hz), 8.36(1H, d, J=3.1Hz), 8.76–8.80(2H, m), 8.83(1H, brs) |
| 36 | δ: 1.34(3H, t, J=7.3Hz), 3.62–3.68(2H, m), 6.49(1H, dd, J=7.9, 4.9Hz), 7.39–7.40(2H, m), 7.62(1H, dd, J=7.9, 1.8Hz), 8.36(1H, dd, J=4.9, 1.8Hz), 8.76–8.78(2H, m), 8.88(1H, brs) |
| 37 | δ: 2.54(1H, d, J=3.7Hz), 6.14(1H, d, J=3.1Hz), 7.25–7.32(3H, m), 7.37(1H, s), 7.71(1H, d, J=7.9Hz), 8.23(1H, d, J=7.9Hz) |
| 38 | δ: 3.10(1H, s), 6.08(1H, s), 7.20(1H, t, J=7.9Hz), 7.26(1H, d, J=7.9Hz), 7.43(1H, d, J=7.9Hz), 7.51(1H, s), 7.68(1H, d, J=7.9Hz), 8.21(1H, d, J=7.9Hz) |
| 39 | δ: 7.46(1H, t, J=7.9Hz), 7.63–7.65(3H, m), 7.93(1H, d, J=7.3Hz) |
| 40 | δ: 7.40(1H, t, J=7.9Hz), 7.67(1H, d, J=7.9Hz), 7.77–7.81(2H, m), 7.90–7.98(2H, m) |
| 41 | δ: 1.31(3H, t, J=7.3Hz), 3.62–3.68(2H, m), 6.82(1H, d, J=7.9Hz), 7.38(1H, d, J=7.9Hz), 7.41–7.46(2H, m), 7.53–7.57(2H, m), 8.65(1H, brs) |
| 42 | δ: 1.31(3H, t, J=7.3Hz), 3.62–3.67(2H, m), 6.82(1H, d, J=7.9Hz), 7.35–7.38(1H, m), 7.50(1H, d, J=7.3Hz), 7.69–7.73(2H, m), 7.83(1H, d, J=7.9Hz), 8.65(1H, brs) |
| 43 | δ: 1.26(3H, t, J=7.4Hz), 3.42(6H, s), 3.57(2H, m), 5.13(1H, brs), 5.14(1H, s), 6.84(1H, d, J=7.8Hz), 7.66(1H, d, J=7.8Hz) |
| 44 | δ: 1.35(3H, t, J=7.4Hz), 3.73(2H, m), 7.12(1H, d, J=7.8Hz), 7.40–7.60(4H, m), 7.85(1H, d, J=7.8Hz), 8.64(1H, brs), 9.94(1H, s) |
| 45 | δ: 1.20(3H, t, J=7.6Hz), 2.57(2H, q, J=7.6Hz), 6.24(1H, d, J=7.2Hz), 7.47–7.54(1H, m), 7.62–7.68(2H, m), 7.77(1H, d, J=7.2Hz), 12.13(1H, brs) |
| 46 | δ: 6.82(1H, brs), 7.50–7.59(4H, m), 7.66–7.78(3H, m), 7.82–7.92(3H, m), 12.33(1H, brs) |
| 47 | δ: 0.90–1.00(2H, m), 1.05–1.15(2H, m), 1.90–2.00(1H, m), 6.00(1H, brs), 7.49(1H, t, J=8.0Hz), 7.60–7.68(3H, m), 7.72(1H, d, J=8.0Hz), 12.2(1H, brs) |
| 48 | δ: 1.24(3H, t, J=7.9Hz), 2.43(3H, s), 2.80(2H, q, J=7.9Hz), 7.19(1H, d, J=7.8Hz), 7.27(2H, d, J=7.2Hz), 7.39(1H, t, J=7.9Hz), 7.51–7.57(1H, m), 7.59–7.64(1H, m), 7.66–7.72(1H, m), 7.76(2H, d, J=7.9Hz), 7.84(1H, d, J=7.2Hz) |
| 49 | δ: 2.44(3H, s), 7.28(1H, d, J=8.8Hz), 7.35–7.50(4H, m), 7.52–7.58(1H, m), 7.63–7.68(1H, m), 7.73–7.80(4H, m), 7.83–7.88(2H, m), 7.99(1H, d, J=8.0Hz) |
| 50 | δ: 0.86–0.93(2H, m), 0.97–1.04(2H, m), 1.95–2.04(1H, m), 2.44(3H, s), 7.20(1H, d, J=8.0Hz), 7.28(2H, d, J=8.0Hz), 7.39(1H, t, J=8.0Hz), 7.50–7.75(5H, m), 7.79(1H, d, J=8.0Hz) |
| 51 | δ: 1.29(3H, t, J=7.2Hz), 1.31(3H, t, J=7.3Hz), 2.70(2H, q, J=7.6Hz), 3.62–3.70(2H, m), 6.34(1H, d, J=7.6Hz), 7.35–7.54(4H, m), 7.57(1H, d, J=7.6Hz), 8.83(1H, brs) |
| 52 | δ: 1.38(3H, t, J=7.6Hz), 3.73–3.82(2H, m), 6.98(1H, d, J=8.0Hz), 7.37–7.53(6H, m), 7.56–7.59(1H, m), 7.75(1H, d, J=8.0Hz), 8.08–8.14(1H, m), 8.87(1H, brs) |
| 53 | δ: 0.95–1.05(2H, m), 1.14–1.20(2H, m), 1.27(3H, t, J=7.2Hz), 1.88–1.98(1H, m), 3.52–3.62(2H, m), 6.39(1H, d, J=7.6Hz), 7.34–7.54(5H, m), 8.84(1H, brs) |
| 54 | δ: 0.87–1.97(15H, m), 2.71(2H, q, J=7.6Hz), 3.72–3.77(1H, m), 6.25(1H, d, J=7.6Hz), 8.19(1H, d, J=7.6Hz), 13.59(1H, brs) |
| 55 | δ: 0.86–1.96(12H, m), 2.44(3H, s), 3.69–3.76(1H, m), 6.24(1H, d, J=7.2Hz), 8.17(1H, d, J=7.2Hz), 13.62(1H, brs) |
| 56 | δ: 0.87–1.89(18H, m), 2.67(2H, q, J=7.6Hz), 3.21–3.38(1H, m), 3.54–3.61(2H, m), 6.36(1H, d, J=8.0Hz), 7.89(1H, d, J=8.0Hz), 9.08(1H, brs) |
| 57 | δ: 0.92(3H, d, J=6.8Hz), 1.01–1.89(12H, m), 2.41(3H, s), 3.20–3.27(1H, m), 3.53–3.61(2H, m), 6.36(1H, d, J=8.0Hz), 7.88(1H, d, J=8.0Hz), 9.09(1H, brs) |
| 58 | δ: 2.64(3H, s), 7.24(1H, d, J=7.3Hz), 7.43(1H, t, J=7.9Hz), 7.60(1H, m), 7.65(2H, m), 7.78(1H, s) |
| 59 | δ: 2.40(3H, s), 2.63(3H, s), 7.22(1H, d, J=7.3Hz), 7.36(1H, t, J=7.3Hz), 7.43(1H, d, J=7.3Hz), 7.57(1H, d, J=7.3Hz), 7.60–7.65(2H, m) |
| 60 | δ: 1.04(3H, t, J=7.6Hz), 1.67–1.76(2H, m), 2.04(3H, s), 3.55–3.60(2H, m), 6.33(1H, d, J=8.0Hz), 7.36–7.57(5H, m), 8.93(1H, brs) |
| 61 | δ: 0.36–0.40(2H, m), 0.60–0.65(2H, m), 1.17–1.27(1H, m), 2.49(3H, s), 3.53(2H, dd, J=7.2, 5.2Hz), 6.34(1H, d, J=7.6Hz), 7.36–7.58(5H, m), 8.99(1H, brs) |
| 62 | δ: 1.04(3H, t, J=7.6Hz), 1.66–1.76(2H, m), 2.40(3H, s), 2.43(3H, s), 3.55–3.60(2H, m), 6.31(1H, d, J=8.0Hz), 7.31–7.36(4H, m), 7.61(1H, d, J=8.0Hz), 8.94(1H, brs) |
| 63 | δ: 0.06–0.38(2H, m), 0.57–0.61(2H, m), 1.14–1.24(1H, m), 2.43(3H, s), 2.45(3H, s), 3.50(2H, dd, J=7.0, 5.0Hz), 6.35(1H, d, J=8.0Hz), 7.33–7.37(4H, m), 7.65(1H, d, J=8.0Hz), 9.03(1H, brs) |
| 64 | δ: 2.63(3H, s), 7.22(1H, d, J=7.6Hz), 7.46–7.50(2H, m), 7.60–7.66(2H, m), 7.79–7.82(2H, m) |
| 65 | δ: 2.67(3H, s), 7.30(1H, d, J=7.6Hz), 7.72(1H, t, J=7.6Hz), 8.13–8.16(1H, m), 8.46–8.49(1H, m), 8.59–8.60(1H, m) |
| 66 | δ: 1.32(3H, t, J=7.4Hz), 2.46(3H, s), 3.63–3.70(2H, m), 6.35(1H, d, J=8.0Hz), 7.49(1H, d, J=8.0Hz), 7.66(1H, t, J=8.0Hz), 7.87(1H, dt, J=8.0, 1.3Hz), 8.35–8.40(2H, m), 8.88(1H, brs) |
| 67 | δ: 1.95(3H, s), 6.15(1H, s), 7.40–7.60(5H, m), 7.80–8.00(3H, m), 8.13(1H, m) |
| 68 | δ: 2.33(3H, s), 2.56(3H, s), 7.04(2H, d, J=8.4Hz), 7.18(1H, d, J=7.2Hz), 7.41(1H, dd, J=8.2, 7.2Hz), 7.45–7.60(5H, m), 7.86(1H, m), 7.90–8.00(2H, m), 8.45(1H, m) |
| 69 | δ: 1.37(3H, t, J=7.4Hz), 2.41(3H, s), 3.71(2H, m), 6.19(1H, d, J=8.4Hz), 7.34(1H, d, J=8.0Hz), 7.35–7.55(4H, m), 7.81(1H, d, J=8.4Hz), 7.85–7.95(2H, m), 9.23(1H, brs) |

TABLE 4

| Ex. No. | DATA |
|---|---|
| 1 | mp.: 141–142° C. (AcOEt-hexane) |
| | Anal.: $C_{17}H_{16}N_3OCl$ |
| |         C (%)    H (%)    N (%)    Cl (%) |
| | calcd.  65.07    5.14    13.39    11.30 |
| | found   65.12    5.01    13.37    11.41 |
| 2 | mp.: 130–132° C. (AcOEt-hexane) |
| | Anal.: $C_{17}H_{16}N_3OBr$ |
| |         C (%)    H (%)    N (%)    Br (%) |
| | calcd.  57.00    4.50    11.73    22.30 |
| | found   57.09    4.67    11.77    22.58 |
| 3 | mp.: 152–153° C. (AcOEt-hexane) |
| | Anal.: $C_{16}H_{14}N_3OCl$ |
| |         C (%)    H (%)    N (%)    Cl (%) |
| | calcd.  64.11    4.71    14.02    11.83 |
| | found   63.98    4.69    14.03    12.11 |
| 4 | mp.: 159–160° C. (AcOEt-hexane) |
| | Anal.: $C_{16}H_{14}N_3OBr$ |
| |         C (%)    H (%)    N (%)    Br (%) |
| | calcd.  55.83    4.10    12.21    23.21 |
| | found   55.91    4.02    12.28    23.44 |
| 5 | mp.: 140–142° C. (AcOEt-hexane) |
| | Anal.: $C_{17}H_{17}N_3O$ |
| |         C (%)    H (%)    N (%) |
| | calcd.  73.10    6.13    15.04 |
| | found   73.00    6.01    14.95 |
| 6 | mp.: 193–195° C. (AcOEt-hexane) |
| | Anal.: $C_{13}H_{19}N_3O$ |
| |         C (%)    H (%)    N (%) |
| | calcd.  73.70    6.53    14.32 |
| | found   73.98    6.46    14.32 |
| 7 | mp.: 163–165° C. (AcOEt-hexane) |
| | Anal.: $C_{16}H_{21}N_3O$ |
| |         C (%)    H (%)    N (%) |
| | calcd.  70.82    7.80    15.48 |
| | found   70.98    7.94    15.54 |
| 8 | mp.: 153–155° C. (AcOEt-hexane) |
| | Anal.: $C_{15}H_{19}N_3O$ |
| |         C (%)    H (%)    N (%) |
| | calcd.  70.01    7.44    16.33 |
| | found   69.99    7.36    16.33 |

TABLE 4-continued

| Ex. No. | DATA | | | | |
|---|---|---|---|---|---|
| 9 | mp.: 205–208° C. (AcOEt) | | | | |
| | Anal.: $C_{13}H_{11}N_3OS$ | | | | |
| | | C (%) | H (%) | N (%) | S (%) |
| | calcd. | 60.68 | 4.31 | 16.33 | 12.46 |
| | found | 60.86 | 4.38 | 16.40 | 12.55 |
| 10 | mp.: 191–194° C. (AcOEt—iPr$_2$O) | | | | |
| | Anal.: $C_{13}H_{11}N_3OS$ | | | | |
| | | C (%) | H (%) | N (%) | S (%) |
| | calcd. | 60.68 | 4.31 | 16.33 | 12.46 |
| | found | 60.74 | 4.18 | 16.40 | 12.70 |
| 11 | mp.: 248–250° C. (AcOEt) | | | | |
| | Anal.: $C_{12}H_{10}N_4OS$ | | | | |
| | | C (%) | H (%) | N (%) | S (%) |
| | calcd. | 55.80 | 3.90 | 21.69 | 12.41 |
| | found | 55.65 | 3.81 | 21.65 | 12.46 |
| 12 | mp.: 172–175° C. (AcOEt—iPr$_2$O) | | | | |
| | Anal.: $C_{14}H_{12}N_4O$ | | | | |
| | | C (%) | H (%) | N (%) | |
| | calcd. | 66.65 | 4.79 | 22.21 | |
| | found | 66.77 | 4.78 | 22.22 | |
| 13 | mp.: 177–179° C. (AcOEt—iPr$_2$O) | | | | |
| | Anal.: $C_{14}H_{12}N_4O$ | | | | |
| | | C (%) | H (%) | N (%) | |
| | calcd. | 66.65 | 4.79 | 22.21 | |
| | found | 66.65 | 4.79 | 22.21 | |
| | found | 66.78 | 4.89 | 22.30 | |
| 14 | mp.: 195–200° C. (AcOEt—iPr$_2$O) | | | | |
| | Anal.: $C_{14}H_{12}N_4O$ | | | | |
| | | C (%) | H (%) | N (%) | |
| | calcd. | 66.65 | 4.79 | 22.21 | |
| | found | 66.57 | 4.70 | 22.08 | |
| 15 | mp.: 177–180° C. (AcOEt-hexane) | | | | |
| | Anal.: $C_{16}H_{11}N_3OClF_3$ | | | | |
| | | C (%) | H (%) | N (%) | Cl (%) | F (%) |
| | calcd. | 54.33 | 3.13 | 11.88 | 10.02 | 16.11 |
| | found | 54.41 | 3.13 | 11.92 | 9.92 | 16.27 |
| 16 | mp.: 148–149° C. (AcOEt-hexane) | | | | |
| | Anal.: $C_{16}H_{11}N_3OBrF_3$ | | | | |
| | | C (%) | H (%) | N (%) | Br (%) | F (%) |
| | calcd. | 48.26 | 2.78 | 10.55 | 20.07 | 14.31 |
| | found | 48.34 | 2.75 | 10.61 | 19.98 | 14.52 |
| 17 | mp.: 195–197° C. (CHCl$_3$—AcOEt) | | | | |
| | Anal.: $C_{16}H_{12}N_3O_2Cl$ | | | | |
| | | C (%) | H (%) | N (%) | Cl (%) |
| | calcd. | 61.25 | 3.86 | 13.39 | 11.30 |
| | found | 61.05 | 3.82 | 13.20 | 11.43 |
| 18 | mp.: 200–203° C. (dec.)(CH$_3$CN—EtOH) | | | | |
| | Anal.: $C_{16}H_{14}N_3O_2Cl$ | | | | |
| | | C (%) | H (%) | N (%) | Cl (%) |
| | calcd. | 60.86 | 4.47 | 13.31 | 11.23 |
| | found | 60.91 | 4.45 | 13.42 | 11.14 |
| 19 | mp.: 198–199.5° C. (CHCl$_3$—Et$_2$O) | | | | |
| | Anal.: $C_{17}H_{16}N_3O_2Cl$ | | | | |
| | | C (%) | H (%) | N (%) | Cl (%) |
| | calcd. | 61.92 | 4.89 | 12.74 | 10.75 |
| | found | 61.63 | 4.90 | 12.63 | 11.01 |
| 20 | mp.: 214–217° C. (CHCl$_3$—Et$_2$O) | | | | |
| | Anal.: $C_{17}H_{14}N_3O_2Cl$ | | | | |
| | | C (%) | H (%) | N (%) | Cl (%) |
| | calcd. | 62.30 | 4.31 | 12.82 | 10.82 |
| | found | 62.50 | 4.35 | 12.80 | 10.90 |
| 21 | mp.: 183–185° C. (EtOH) | | | | |
| | Anal.: $C_{21}H_{16}N_3OCl$ | | | | |
| | | C (%) | H (%) | N (%) | Cl (%) |
| | calcd. | 69.71 | 4.46 | 11.61 | 9.80 |
| | found | 69.71 | 4.48 | 11.51 | 9.67 |
| 22 | mp.: 182–184° C. (CHCl$_3$-hexane) | | | | |
| | Anal.: $C_{18}H_{16}N_3OCl$ | | | | |
| | | C (%) | H (%) | N (%) | Cl (%) |
| | calcd. | 66.36 | 4.95 | 12.90 | 10.88 |
| | found | 66.30 | 4.97 | 12.92 | 11.01 |
| 23 | mp.: 122–124° C. (AcOEt-hexane) | | | | |
| | Anal.: $C_{17}H_{15}N_3OBrCl$ | | | | |
| | | C (%) | H (%) | N (%) | Cl (%) | Br (%) |
| | calcd. | 52.00 | 3.85 | 10.70 | 9.03 | 20.35 |
| | found | 52.00 | 3.74 | 10.71 | 9.29 | 20.06 |
| 24 | mp.: 106–108° C. (AcOEt-hexane) | | | | |
| | Anal.: $C_{19}H_{13}N_3O_3Cl$ | | | | |
| | | C (%) | H (%) | N (%) | Cl (%) |
| | calcd. | 61.38 | 4.88 | 11.30 | 9.53 |
| | found | 61.33 | 4.77 | 11.23 | 9.79 |
| 25 | mp.: 198–199.5° C. (CHCl$_3$—Et$_2$O) | | | | |
| | Anal.: $C_{17}H_{16}N_3O_2Cl$ | | | | |
| | | C (%) | H (%) | N (%) | Cl (%) |
| | calcd. | 61.92 | 4.89 | 12.74 | 10.75 |
| | found | 61.63 | 4.90 | 12.63 | 11.01 |
| 26 | mp.: 112–115° C. (iPr$_2$O-hexane) | | | | |
| | Anal.: $C_{17}H_{23}N_3O$ | | | | |
| | | C (%) | H (%) | N (%) | |
| | calcd. | 71.55 | 8.12 | 14.72 | |
| | found | 71.51 | 8.32 | 14.71 | |
| 27 | mp.: 100–102° C. (iPr$_2$O-hexane) | | | | |
| | Anal.: $C_{18}H_{25}N_3O$ | | | | |
| | | C (%) | H (%) | N (%) | |
| | calcd. | 72.21 | 8.42 | 14.03 | |
| | found | 72.04 | 8.42 | 13.86 | |
| 28 | mp.: 195–200° C. (AcOEt—iPr$_2$O) | | | | |
| | Anal.: $C_{16}H_{14}N_3SCl$ | | | | |
| | | C (%) | H (%) | N (%) | Cl (%) | S (%) |
| | calcd. | 60.85 | 4.47 | 13.30 | 11.23 | 10.15 |
| | found | 60.72 | 4.46 | 13.29 | 11.20 | 10.19 |
| 29 | mp.: 174–175° C. (EtOH) | | | | |
| | Anal.: $C_{17}H_{16}N_3OBr$ | | | | |
| | | C (%) | H (%) | N (%) | Br (%) |
| | calcd. | 57.00 | 4.50 | 11.73 | 22.30 |
| | found | 56.89 | 4.44 | 11.93 | 22.50 |
| 30 | mp.: 152–155° C. (AcOEt—iPr$_2$O) | | | | |
| | Anal.: $C_{17}H_{16}N_3OCl$ | | | | |
| | | C (%) | H (%) | N (%) | Cl (%) |
| | calcd. | 65.07 | 5.14 | 13.39 | 11.30 |
| | found | 65.07 | 5.09 | 13.38 | 11.21 |
| 31 | mp.: 144–146° C. (AcOEt—iPr$_2$O) | | | | |
| | Anal.: $C_{18}H_{16}N_3OCl$ | | | | |
| | | C (%) | H (%) | N (%) | Cl (%) |
| | calcd. | 66.36 | 4.95 | 12.90 | 10.88 |
| | found | 66.21 | 4.78 | 12.97 | 10.62 |
| 32 | mp.: 141–144° C. (AcOEt—iPr$_2$O) | | | | |
| | Anal.: $C_{13}H_{13}N_3O$ | | | | |
| | | C (%) | H (%) | N (%) | |
| | calcd. | 73.70 | 6.53 | 14.32 | |
| | found | 73.67 | 6.51 | 14.18 | |
| 33 | mp.: 124–126° C. (AcOEt—iPr$_2$O) | | | | |
| | Anal.: $C_{19}H_{19}N_3O$ | | | | |
| | | C (%) | H (%) | N (%) | |
| | calcd. | 74.73 | 6.27 | 13.76 | |
| | found | 74.78 | 6.32 | 13.69 | |
| 34 | mp.: 131–133° C. (iPr$_2$O) | | | | |
| | Anal.: $C_{17}H_{23}N_3O$ | | | | |
| | | C (%) | H (%) | N (%) | |
| | calcd. | 71.55 | 8.12 | 14.72 | |
| | found | 71.47 | 8.32 | 14.66 | |
| 35 | mp.: 174–175° C. (AcOEt-hexane) | | | | |
| | Anal.: $C_{17}H_{16}N_3OCl$ | | | | |
| | | C (%) | H (%) | N (%) | Cl (%) |
| | calcd. | 65.07 | 5.14 | 13.39 | 11.30 |
| | found | 64.99 | 5.13 | 13.37 | 11.41 |
| 36 | mp.: 270–275° C. (dec.)(DMF—CH$_3$CN) | | | | |
| | Anal.: $C_{16}H_{13}N_4O_2Cl$ | | | | |
| | | C (%) | H (%) | N (%) | Cl (%) |
| | calcd. | 58.46 | 3.99 | 17.04 | 10.78 |
| | found | 58.43 | 3.93 | 17.13 | 10.76 |
| 37 | mp.: 201–202° C. (AcOEt) | | | | |
| | Anal.: $C_{16}H_{14}N_4O_3$ | | | | |
| | | C (%) | H (%) | N (%) | |
| | calcd. | 61.93 | 4.55 | 18.06 | |
| | found | 61.89 | 4.43 | 18.10 | |
| 38 | mp.: 175–177° C. (AcOEt—iPr$_2$O) | | | | |
| | Anal.: $C_{16}H_{13}N_3OClBr$ | | | | |
| | | C (%) | H (%) | N (%) | Cl (%) | Br (%) |
| | calcd. | 50.75 | 3.46 | 11.10 | 9.36 | 21.10 |
| | found | 50.68 | 3.33 | 11.09 | 9.49 | 20.95 |
| 39 | mp.: 143–144° C. (AcOEt-hexane) | | | | |
| | Anal.: $C_{17}H_{15}N_3OCl_2$ | | | | |
| | | C (%) | H (%) | N (%) | Cl (%) |
| | calcd. | 58.64 | 4.34 | 12.07 | 20.36 |

TABLE 4-continued

| Ex. No. | DATA |
|---|---|
| | found 58.62 4.29 12.07 20.25 |
| 40 | mp.: 140–143° C. (AcOEt-hexane) |
| | Anal.: $C_{19}H_{18}N_3O_2SCl$ |
| |         C (%)    H (%)    N (%)    S (%)    Cl (%) |
| | calcd.   58.83    4.68    10.83    8.27    9.14 |
| | found    59.03    4.49    10.88    8.14    9.30 |
| 41 | mp.: 169–172° C. (AcOEt—iPr$_2$O) |
| | Anal.: $C_{17}H_{16}N_3SCl$ |
| |         C (%)    H (%)    N (%)    S (%)    Cl (%) |
| | calcd.   61.90    4.89    12.74    9.72    10.75 |
| | found    61.94    4.83    12.73    9.80    10.66 |
| 42 | mp.: 196–197° C. (AcOEt) |
| | Anal.: $C_{20}H_{17}N_3O$ |
| |         C (%)    H (%)    N (%) |
| | calcd.   76.17    5.43    13.32 |
| | found    76.23    5.49    13.40 |
| 43 | mp.: 99–100° C. (iPr$_2$O) |
| | Anal.: $C_{19}H_{20}N_3O_3Cl$ |
| |         C (%)    H (%)    N (%)    Cl (%) |
| | calcd.   61.04    5.39    11.24    9.48 |
| | found    60.91    5.36    11.15    9.65 |

In the following Tables 5, 6, and 7, chemical structures of the compounds obtained in Examples are shown using tables and with classification depending on the types of the compounds.

In the Tables, Ex. No., Et, iPr, and Ac are as described above, and Me means a methyl group, nPr means a normal propyl group, cPr means a cyclopropyl group, cHex means a cyclohexyl group, Ph means a phenyl group, Naph means a naphthyl group, and Py means a pyridyl group.

TABLE 5

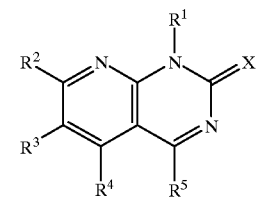

| Ex. No. | $R^1$ | $R^2$ | $R^6$ |
|---|---|---|---|
| 1 | Et | Et | Cl |
| 2 | Et | Et | Br |
| 3 | Et | Me | Cl |
| 4 | Et | Me | Br |
| 5 | Et | Me | Me |
| 6 | Et | Et | Me |
| 30 | nPr | Me | Cl |
| 32 | nPr | Me | Me |

TABLE 6

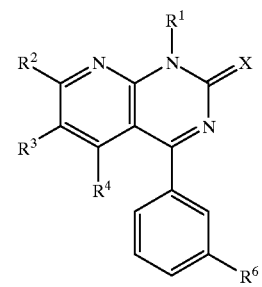

| Ex. No. | $R^1$ | $R^2$ | $R^3$ | $R^4$ | $R^6$ | X |
|---|---|---|---|---|---|---|
| 15 | Et | —CF$_3$ | H | H | Cl | O |
| 16 | Et | —CF$_3$ | H | H | Br | O |
| 17 | Et | —CHO | H | H | Cl | O |
| 18 | Et | —CH$_2$OH | H | H | Cl | O |
| 19 | Et | —CH(OH)CH$_3$ | H | H | Cl | O |
| 20 | Et | Ac | H | H | Cl | O |
| 21 | Et | Ph | H | H | Cl | O |
| 22 | Et | cPr | H | H | Cl | O |
| 23 | Et | —CHBrCH | H | H | Cl | O |
| 24 | Et | —CH(OAc)CH$_3$ | H | H | Cl | O |
| 25 | Et | —CH(OH)CH$_3$ | H | H | Cl | O |
| 28 | Et | Me | H | H | Cl | S |
| 29 | Et | Me | Me | H | Br | O |
| 31 | —CH$_2$-cPr | Me | H | H | Cl | O |
| 33 | —CH$_2$-cPr | Me | H | H | Me | O |
| 35 | Et | Me | Cl | H | Me | O |
| 36 | Et | —CH=N~OH | H | H | Cl | O |
| 37 | Et | Me | H | H | NO$_2$ | O |
| 38 | Et | —CH$_2$Br | H | H | Cl | O |
| 39 | Et | Et | Cl | H | Cl | O |
| 40 | Et | —CH(SAc)CH$_3$ | H | H | Cl | O |
| 41 | Et | Et | H | H | Cl | O |
| 43 | Et | —C(OMe)$_2$CH$_3$ | H | H | Cl | O |

TABLE 7

| Ex. No. | $R^1$ | $R^2$ | $R^3$ | $R^4$ | $R^5$ | X |
|---|---|---|---|---|---|---|
| 7 | Et | Me | H | H | cHex | O |
| 8 | Et | H | H | H | cHex | O |
| 9 | Et | H | H | H | 2-Thienyl | O |
| 10 | Et | H | H | H | 3-Thienyl | O |
| 11 | Et | H | H | H | 2-Thiazolyl | O |
| 12 | Et | H | H | H | 2-Py | O |
| 13 | Et | H | H | H | 3-Py | O |
| 14 | Et | H | H | H | 4-Py | O |
| 26 | Et | Me | H | H | 3-Me-cHex | O |
| 27 | Et | Et | H | H | 3-Me-cHex | O |
| 34 | Et | Et | H | H | cHex | O |
| 42 | Et | Me | H | H | 1-Naph | O |

In addition to the above-described compounds of Examples, other compounds of the present invention will be shown in the following Table 8 and 9. These compounds can be synthesized, without particular experiments, in accordance with any one of the above-described preparation pathway and processes described in Production Methods and Examples and modified processes thereof known to those ordinary skilled in the art.

Some compounds shown in Table 8 as various types of tisomers. All of these isomers as mixtures or isolated forms are included in the present invention. In the Tables, Me, Et, nPr, iPr, cPr, cHex, Ac, Ph, Naph, and Py are as described above, and Compnd. No. means Compound Number, cBu means a cyclobutyl group, cPe means a cyclopentyl group, and cHep means a cycloheptyl group, respectively.

TABLE 8

| Compnd. No. | R¹ | R² | R³ | R⁴ | R⁵ | X |
|---|---|---|---|---|---|---|
| 1 | Et | Et | H | H | CF₃ | O |
| 2 | Et | Me | H | H | CF₃ | O |
| 3 | Et | Et | H | H | OH | O |
| 4 | Et | Me | H | H | OH | O |
| 5 | Et | Et | H | H | OMe | O |
| 6 | Et | Me | H | H | OMe | O |
| 7 | Et | Et | H | H | CN | O |
| 8 | Et | Me | H | H | CN | O |
| 9 | Et | Et | H | H | NO₂ | O |
| 10 | Et | Et | H | H | F | S |
| 11 | Et | Me | H | H | F | S |
| 12 | Et | Et | H | H | Br | S |
| 13 | Et | Me | H | H | Br | S |
| 14 | Et | Et | H | H | Me | S |
| 15 | Et | Me | H | H | Me | S |
| 16 | Et | Et | H | H | CF₃ | S |
| 17 | Et | Me | H | H | CF₃ | S |
| 18 | Et | Et | H | H | OH | S |
| 19 | Et | Me | H | H | OH | S |
| 20 | Et | Et | H | H | OMe | S |
| 21 | Et | Me | H | H | CMe | S |
| 22 | Et | Et | H | H | CN | S |
| 23 | Et | Me | H | H | CN | S |
| 24 | Et | Et | H | H | NO₂ | S |
| 25 | Et | Me | H | H | NO₂ | S |
| 26 | Et | F | H | H | Cl | O |
| 27 | Et | F | H | H | Cl | S |
| 28 | Et | Cl | H | H | Cl | O |
| 29 | Et | Cl | H | H | Cl | S |
| 30 | Et | Br | H | H | Cl | O |
| 31 | Et | Br | H | H | Cl | S |
| 32 | nPr | cPr | H | H | Cl | O |
| 33 | nPr | cPr | H | H | Cl | S |
| 34 | Et | cPr | H | H | Cl | S |
| 35 | Et | cPr | H | H | Br | O |
| 36 | Et | cPr | H | H | Br | S |
| 37 | Et | cPr | H | H | Me | O |
| 38 | Et | cPr | H | H | Me | S |
| 39 | Et | cBu | H | H | Cl | O |
| 40 | Et | cBu | H | H | Cl | S |
| 41 | Et | cPe | H | H | Cl | O |
| 42 | Et | cPe | H | H | Cl | S |
| 43 | Et | cHex | H | H | Cl | O |
| 44 | Et | cHex | H | H | Cl | S |
| 45 | Et | cHep | H | H | Cl | O |
| 46 | Et | cHep | H | H | Cl | S |
| 47 | Et | —CHFCH₃ | H | H | Cl | O |
| 48 | Et | —CHFCH₃ | H | H | Cl | S |
| 49 | Et | —CHClCH₃ | H | H | Cl | O |
| 50 | Et | —CHClCH₃ | H | H | Cl | S |
| 51 | Et | CH(OH)CH₃ | H | H | Cl | S |
| 52 | Et | CH(OH)CH₃ | H | H | Br | O |
| 53 | Et | CH(OH)CH₃ | H | H | Br | S |

TABLE 8-continued

| Compnd. No. | R¹ | R² | R³ | R⁴ | R⁵ | X |
|---|---|---|---|---|---|---|
| 54 | Et | —CH(OH)CH₃ | H | H | Me | O |
| 55 | Et | —CH(OH)CH₃ | H | H | Me | S |
| 56 | Et | —CH₂CAc | H | H | Cl | O |
| 57 | Et | —CH₂OAc | H | H | Cl | S |
| 58 | Et | —CH(SAc)CH₃ | H | H | Cl | S |
| 59 | Et | —CH(SAC)CH₃ | H | H | Br | O |
| 60 | Et | —CH(SAc)CH₃ | H | H | Br | S |
| 61 | Et | —CH=N~OH | H | H | Cl | S |
| 62 | Et | —CH=N~OH | H | H | Br | O |
| 63 | Et | —CH=N~OH | H | H | Br | S |
| 64 | Et | —CH=N~OH | H | H | Me | O |
| 65 | Et | —CH=N~OH | H | H | Me | S |
| 66 | Et | —CH=N~OMe | H | H | Cl | O |
| 67 | Et | —CH=N~OMe | H | H | Cl | S |

TABLE 9

| Compnd. No. | R¹ | R² | R³ | R⁴ | R⁶ | X |
|---|---|---|---|---|---|---|
| 68 | Et | cPr | H | H | cHex | O |
| 69 | Et | cPr | H | H | cHex | S |
| 70 | Et | CF₃ | H | H | cHex | O |
| 71 | Et | CF₃ | H | H | cHex | S |
| 72 | Et | —CHBrCH₃ | H | H | cHex | O |
| 73 | Et | —CHBrCH₃ | H | H | cHex | S |
| 74 | Et | —CH(OH)CH₃ | H | H | cHex | O |
| 75 | Et | —CH(OH)CH₃ | H | H | cHex | S |
| 76 | Et | —CH(SAc)CH₃ | H | H | cHex | O |
| 77 | Et | —CH(SAc)CH₃ | H | H | cHex | S |
| 78 | Et | —CH=N~OH | H | H | cHex | O |
| 79 | Et | —CH=N~OH | H | H | cHex | O |
| 80 | Et | cPr | H | H | 3-Me-cHex | O |
| 81 | Et | cPr | H | H | 3-Me-cHex | S |
| 82 | Et | CF₃ | H | H | 3-Me-cHex | O |
| 83 | Et | CF₃ | H | H | 3-Me-cHex | S |
| 84 | Et | —CHBrCH₃ | H | H | 3-Me-cHex | O |
| 85 | Et | —CHBrCH | H | H | 3-Me-cHex | H |
| 86 | Et | —CH(OH)CH | H | H | 3-Me-cHex | O |
| 87 | Et | —CH(CH)CH | H | H | 3-Me-cHex | S |
| 88 | Et | —CH(SAc)CH₃ | H | H | 3-Me-cHex | O |
| 89 | Et | —CH(SAc)CH₃ | H | H | 3-Me-cHex | S |
| 90 | Et | —CH=N~OH | H | H | 3-Me-cHex | O |
| 91 | Et | —CH=N~OH | H | H | 3-Me-cHex | S |
| 92 | Et | Et | H | H | 3-Cl-cHex | O |
| 93 | Et | Et | H | H | 3-Cl-cHex | S |
| 94 | Et | Et | H | H | 3-Br-cHex | O |
| 95 | Et | Et | H | H | 3-Br-cHex | S |
| 96 | Et | Et | H | H | 5-Cl-2-Thienyl | O |

TABLE 9-continued

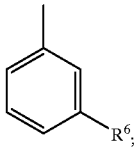

| Compnd. No. | $R^1$ | $R^2$ | $R^3$ | $R^4$ | $R^6$ | X |
|---|---|---|---|---|---|---|
| 97 | Et | Me | H | H | 5-Cl-2-Thienyl | O |
| 98 | Et | Et | H | H | 5-Br-2-Thienyl | O |
| 99 | Et | Me | H | H | 5-Br-2-Thienyl | O |
| 100 | Et | Et | H | H | 5-Me-2-Thienyl | O |
| 101 | Et | Me | H | H | 5-Me-2-Thienyl | O |
| 102 | Et | Et | H | H | 4-Cl-2-Thiazolyl | O |
| 103 | Et | Me | H | H | 4-Cl-2-Thiazolyl | O |
| 104 | Et | Et | H | H | 4-Br-2-Thiazolyl | O |
| 105 | Et | Me | H | H | 4-Br-2-Thiazolyl | O |
| 106 | Et | Et | H | H | 4-Me-2-Thiazolyl | O |
| 107 | Et | Me | H | H | 4-Me-2-Thiazolyl | O |
| 108 | Et | Et | H | H | 6-Cl-2-Py | O |
| 109 | Et | Me | H | H | 6-Cl-2-Py | O |
| 110 | Et | Et | H | H | 6-Br-2-Py | O |
| 111 | Et | Me | H | H | 6-Br-2-Py | O |
| 112 | Et | Et | H | H | 6-Me-2-Py | O |
| 113 | Et | Me | H | H | 6-Me-2-Py | O |
| 114 | Et | Et | H | H | 2-Cl-6-Pyrimidinyl | O |
| 115 | Et | Me | H | H | 2-Cl-6-Pyrimidinyl | O |
| 116 | Et | Et | H | H | 2-Br-6-Pyrimidinyl | O |
| 117 | Et | Me | H | H | 2-Br-6-Pyrimidinyl | O |
| 118 | Et | Et | H | H | 2-Me-6-Pyrimidinyl | O |
| 119 | Et | Me | H | H | 2-Me-6-Pyrimidinyl | O |
| 120 | Et | Et | H | H | 4-Benzofuryl | O |
| 121 | Et | Me | H | H | 4-Benzofuryl | O |
| 122 | Et | Et | H | H | 4-Benzothienyl | O |
| 123 | Et | Me | H | H | 4-Benzothienyl | O |
| 124 | Et | Et | H | H | 4-Benzoxazolyl | O |
| 125 | Et | Me | H | H | 4-Benzoxazolyl | O |
| 126 | Et | Et | H | H | 4-Benzothiazolyl | O |
| 127 | Et | Me | H | H | 4-Benzothiazolyl | O |
| 128 | Et | Et | H | H | 5-Quinolyl | O |
| 129 | Et | Me | H | H | 5-Quinolyl | O |

We claim:

1. A pyrido[2,3-d]pyrimidine compound represented by the following formula (III) or a pharmaceutically acceptable salt thereof:

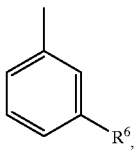

(III)

in the above formula, wherein

X: an oxygen atom or a sulfur atom, $R^1$: a lower alkyl group, a cycloalkyl-lower alkyl group or a cycloalkyl group, $R^3$: a hydrogen atom, a halogen atom or a lower alkyl group $R^4$: a hydrogen atom or a lower alkyl group, $R^5$: a cycloalkyl group which may be substituted with the same group of $R^6$; a naphthyl group which may be substituted with the same group of $R^6$; a five- or six-membered monocyclic hetero ring group having 1 to 4 hetero atoms selected from the group consisting of a nitrogen atom, an oxygen atom and a sulfur atom, which may be substituted with the same group of $R^6$ and which may be condensed with a benzene ring; or a group represented by the formula

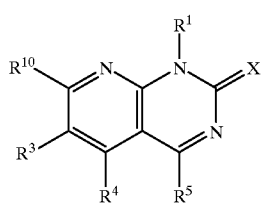

and $R^6$: a halogen atom, a lower alkyl group, a halogeno-lower alkyl group, a hydroxyl group, a lower alkoxy group, a cyano group or a nitro group, $R^{10}$: a hydrogen atom, a halogen atom, a lower alkyl group, a halogeno-lower alkyl group, a hydroxy-lower alkyl group, a mercapto-lower alkyl group, a lower alkoxy-lower alkyl group, a lower alkylthio-lower alkyl group, a lower alkanoyloxy-lower alkyl group, a lower alkanoylthio-lower alkyl group, a lower alkanoyl-lower alkyl group, a hydroxyimino-lower alkyl group, a lower alkoxyimino-lower alkyl group, a cycloalkyl group, an aryl group or a lower alkanoyl group, with the proviso that $R^{10}$ is a group other than a hydrogen atom and a lower alkyl group when $R^5$ is a group represented by the formula $R^6$ is a halogen atom, a lower alkyl group or a lower alkoxy group, $R^1$ is a lower alkyl group or a cycloalkyl group, $R^3$ and $R^4$ are both a hydrogen atom and X is an oxygen atom.

2. The compound according to claim 1, wherein $R^{10}$ is a hydrogen atom, a lower alkyl group, a halogeno-lower alkyl group, a hydroxy-lower alkyl group, a mercapto-lower alkyl group, a lower alkoxy-lower alkyl group, a lower alkylthio lower alkyl group, a lower alkanoyloxy-lower alkyl group, a lower alkanoylthio-lower alkyl group, a hydroxyimino-lower alkyl group, a cycloalkyl group, an aryl group or a lower alkanoyl group.

3. The compound according to claim 2, wherein $R^{10}$ is a hydrogen atom, a lower alkyl group, a halogeno-lower alkyl group, a hydroxy-lower alkyl group, a lower alkoxy-lower alkyl group, a lower alkanoyloxy-lower alkyl group, a lower alkanoylthio-lower alkyl group, a hydroxyimino-lower alkyl group, a cycloalkyl group, an aryl group or a lower alkanoyl group.

4. The compound according to claim 3, wherein $R^{10}$ is the group of claim 3; $R^4$ is a hydrogen atom; $R^5$ is (1) a cycloalkyl group which may be substituted with a lower alkyl group, (2) a naphthyl group, (3) a five- or six-membered monocyclic hetero ring group having 1 to 4 hetero atoms selected from the group consisting of a nitrogen atom, an oxygen atom and a sulfur atom or (4) a group represented by the formula

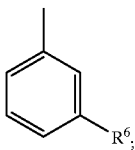

and $R^6$ is a halogen atom, a lower alkyl group, a halogeno-lower alkyl group, a lower alkoxy group, a cyano group or a nitro group.

5. The compound according to claim 4, wherein $R^{10}$ is a lower alkyl group or a cycloalkyl-lower alkyl group, $R^2$ is a lower alkyl group, a halogeno-lower alkyl group, a hydroxy lower alkyl group, a lower alkanoylthio-lower alkyl group, a hydroxyimino-lower alkyl group, a cycloalkyl group or a lower alkanoyl group, $R^3$ and $R^4$ are both a hydrogen atom, $R^5$ is a cycloalkyl group which may be substituted with a lower alkyl group, or a group represented by the formula

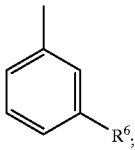

and $R^6$ is a halogen atom, a lower alkyl group or a nitro group.

6. The compound according to claim 5, wherein the compound is selected from the group consisting of 4-cyclohexyl-1-ethyl-7-methylpyrido[2,3-d]pyrimidin-2(1H)-one, 4-(3-chlorophenyl)-1-ethyl-7-(1-hydroxyethyl)pyrido[2,3-d]pyrimidin-2(1H)-one, 4-(3-chlorophenyl)-7-cyclopropyl-1-ethylpyrido[2,3-d]pyrimidin-2(1H)-one, 1-ethyl-7-methyl-4-(3-methylcyclohexyl) pyrido[2,3-d]pyrimidin-2(1H)-one, 1,7-diethyl-4-(3-methylcyclohexyl)pyrido[2,3-d]pyrimidin-2(1H)-one, 4-(3-chlorophenyl)-1-ethyl-7-methylpyrido[2,3-d]pyrimidin-2(1H)-thione, 1-cyclopropylmethyl-7-methyl-4-(3-methylphenyl)pyrido[2,3-d]pyrimidin-2(1H)-one, 4-cyclohexyl-1,7-diethylpyrido[2,3-d]pyrimidin-2(1H)-one, 4-(3-chlorophenyl)-1-ethyl-7-hydroxyiminomethylpyrido[2,3-d]pyrimidin-2(1H)-one, 7-(1-acetylthioethyl)-4-(3-chlorophenyl)-1-ethylpyrido[2,3-d]pyrimidin-2(1H)-one and 1,7-diethyl-4-(3-chlorophenyl)pyrido[2,3-d]pyrimidin-2(1H)-thione.

7. A pyrido[2,3-d]pyrimidine compound or a pharmacutically acceptable salt thereof selected from the group consisting of 4-(3-chlorophenyl)-1,7-diethylpyrido[2,3-d]pyrimidin-2(1H)-one, 4-(3-bromophenyl)-1,7-diethylpyrido[2,3-d]pyrimidin-2(1H)-one, 4-(3-chlorophenyl)-1-ethyl-7-methylpyrido[2,3-d]pyrimidin-2(1H)-one, 4-(3-bromophenyl)-1-ethyl-7-methylpyrido[2,3-d]pyrimidin-2(1H)-one, 1-ethyl-7-methyl-4-(3-methylphenyl)pyrido[2,3-d]pyrimidin-2(1H)-one and 1,7-diethyl-4-(3-methylphenyl)pyrido[2,3-d]pyrimidin-2(1 H)-one.

8. A pharmaceutical composition which comprises a pyrido[2,3-d]pyrimidine derivative according to any one of claims 1–7 or a pharmaceutically acceptable salt thereof, and a pharmaceutically acceptable carrier.

9. A pharmaceutical composition for a type IV phosphodiesterase inhibitor which comprises a pyrido[2,3-d]pyrimidine derivative according to any one of claims 1 to 7 or a pharmaceutically acceptable salt thereof, and a pharmaceutically acceptable carrier.

10. A method for treating a respiratory disease associated with type IV phosphodiesterase activity selected from the group consisting of bronchial asthma, chronic bronchitis, pneumonia, and ARDS, which comprises administering a pyrido[2,3-d]pyrimidine derivative described in any one of claims 1–7, or a pharmaceutically acceptable salt thereof, in an effective amount for treating said disease in a patient suffering from or susceptible to said disease.

11. The method according to claim 10, wherein said respiratory disease associated with type IV phosphodiesterase activity is bronchial asthma.

* * * * *